United States Patent
Fischer et al.

(10) Patent No.: US 11,091,561 B2
(45) Date of Patent: Aug. 17, 2021

(54) HER-2 BINDING ANTIBODIES

(71) Applicant: MAB Discovery GmbH, Neuried (DE)

(72) Inventors: Stephan Fischer, Weilheim (DE); Michael Brandt, Munich (DE)

(73) Assignee: MAB DISCOVERY GMBH, Neuried (DE)

( * ) Notice: Subject to any disclaimer, the term of this patent is extended or adjusted under 35 U.S.C. 154(b) by 101 days.

(21) Appl. No.: 16/099,228

(22) PCT Filed: May 8, 2017

(86) PCT No.: PCT/EP2017/060935
§ 371 (c)(1),
(2) Date: Nov. 6, 2018

(87) PCT Pub. No.: WO2017/191327
PCT Pub. Date: Nov. 9, 2017

(65) Prior Publication Data
US 2019/0241674 A1    Aug. 8, 2019

Related U.S. Application Data

(63) Continuation of application No. PCT/EP2017/060935, filed on May 8, 2017.

(30) Foreign Application Priority Data

May 6, 2016 (EP) .................... 16168619.1

(51) Int. Cl.
C07K 16/32 (2006.01)
A61P 35/04 (2006.01)
A61P 35/00 (2006.01)
A61K 39/00 (2006.01)

(52) U.S. Cl.
CPC .............. *C07K 16/32* (2013.01); *A61P 35/00* (2018.01); *A61P 35/04* (2018.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/71* (2013.01); *C07K 2317/73* (2013.01)

(58) Field of Classification Search
CPC ........... C07K 16/32; A61P 35/04; A61P 35/00
USPC ...................................... 424/133.1
See application file for complete search history.

(56) References Cited

U.S. PATENT DOCUMENTS 9,527,913 B2    12/2016 Lantto et al.
9,714,294 B2    7/2017 De Goeij et al.
9,862,769 B2    1/2018 De Goeij et al.
10,174,116 B2   1/2019 Lee et al.
2008/0071063 A1 3/2008 Allan et al.

FOREIGN PATENT DOCUMENTS

EP    0590058 B1    11/2003

OTHER PUBLICATIONS

PCT International Search Report and Written Opinion for PCT Application No. PCT/EP2017/060935 dated Nov. 15, 2017 (25 pages).
Bedard et al., "Beyond Trastuzumab: Overcoming Resistance to Targeted HER-2 Therapy in Breast Cancer," Current Cancer Drug Targets, 2009, 9(2):148-162.
Clynes et al., "Inhibitor Fc Receptors Modulate in vivo Cytoxicity Against Tumor Targets," Nature Medicine, 2000, 6(4):443-446.
Gershoni et al., "Epitope Mapping—The First Step in Developing Epitope-Based Vaccines," BIOD, 2007, 21(3):145-156.
Junttila et al., "Superior in vivo Efficacy of Afucosylated Trastuzumab in the Treatment of HER2-Amplified Breast Cancer," Cancer Research, 2010, 70(11):4481-4489.
Liu et al., "Afucosylated Antibodies Increase Activation of FcyRIIIa-Dependent Signaling Components to Intensify Processes Promoting ADCC," Cancer Immunology Resaerch, 2015, 3(2):173-183.
Rudikoff et al., "Single Amino Acid Substitution Altering Antigen-Binding Specificity," Proc. Natl. Acad. Sc., 1982, 79:1979-1983.
Sorbera et al., "Trastuzumab: Antineoplastic Mab," Drugs of the Future, 1998, 23(10):1078-1082.
Japanese Office Action for JP Application No. 510474/2019 dated Apr. 20, 2021 (English translation, 10 pages).
Meng et al., "A Monoclonal Antibody Targeting ErbB2 Domain III Inhibits ErbB2 Signaling and Suppresses the Growth of ErbB2-Overexpressing Breast Tumors," Oncogenesis, 2016, S, e211, 7 pages.

*Primary Examiner* — Yan Xiao
(74) *Attorney, Agent, or Firm* — Eversheds Sutherland (US) LLP

(57) ABSTRACT

The present invention relates to monoclonal antibodies that specifically bind to HER2, or a fragment or derivative thereof or a polypeptide that contains at least a portion of said antibody that is sufficient to confer specific HER2 binding to the polypeptide. Said antibodies bind to the human Fc receptor and induce FcR mediated signaling pathways. The antibodies according to the invention bind to a different epitope than trastuzumab. The invention also relates to the use of an antibody according to the invention in the treatment of a HER-2 mediated disease. The present invention also relates to a pharmaceutical composition comprising a pharmaceutically acceptable carrier and a therapeutically effective amount of the antibody according to the invention, and the use of said composition in the treatment of a HER-2 mediated disease.

21 Claims, 10 Drawing Sheets
Specification includes a Sequence Listing.

Fig.1:   Sequences (amino acids in one letter code)

VH complete:    SEQ ID NO: 1-6
VL complete:    SEQ ID NO: 7-12

CDR-H1:    SEQ ID NO: 13-18
CDR-H2:    SEQ ID NO: 19-24
CDR-H3:    SEQ ID NO: 25-30
CDR-L1:    SEQ ID NO: 31-36
CDR-L2:    SEQ ID NO: 37-42
CDR-L3:    SEQ ID NO: 43-48

FR-H1:    SEQ ID NO: 49-54
FR-H2:    SEQ ID NO: 55-60
FR-H3:    SEQ ID NO: 61-66
FR-H4:    SEQ ID NO: 67-72

FR-L1:    SEQ ID NO: 73-78
FR-L2:    SEQ ID NO: 79-84
FR-L3:    SEQ ID NO: 85-90
FR-L4:    SEQ ID NO: 91-96

CR-L:    SEQ ID NO: 97
CR-H:    SEQ ID NO: 98-99

VH complete:    SEQ ID NO: 100-101
VL complete:    SEQ ID NO: 102-104

| mAB name | SEQ ID NO. | Complete Heavy-chain VR sequence |
|---|---|---|
| C074 | 1 | QSLEESGGRLVTPGTPLTLTCTVSGFSLSSYNMGWVRQAPGKGLEWIGIISHSDNTYYASWAKGRFTISKTSTTVDLKMTSPTTEDTATYFCARGAAGGSGAYNLWGQGMLVTVSS |
| C031 | 2 | QSVEESGGRLVTPGTPLTLTCTVSGFSLSNYNMAWVRQAPGEGLEYIGIINAGGTAYYASWAKGRITISKTSTTVDLKISSPTAEDTATYFCARSYTSNSGAFNIWGPGTLVTVSS |
| B106 | 3 | QSVEESGGRLVTPGTPLTLTCTVSGFSLSSYAMSWVRQAPGKGLEWIGIIYSGGNAHYASWAKGRFTISRTSTTVDLKMTSLTTEDTATYFCARGDDSSGLRLWGQGTLVTVSS |
| B100 | 4 | QSVEESGGRLVTPGTPLTLTCTVSGFSLSNYGVSWVRQAPGKGLEYIGIISGSGFTYYASWAKGRFTISKTSTTVDLKITSPTTKDTATYFCARGVVPGYNAGGLWGQGTLVTVSS |
| AK57 | 5 | QSVEESGGRLVTPGTPLTLTCTVSGFSLSSYAMSWVRQAPGKGLEWIGIIYAISDNTWFASWAKGRFTISKTSTTVDLKITSPTTEDTATYFCARALYAGYTAGYYFSLWGPGTLVTVSS |
| B115 | 6 | QSLEESGGDLVKPGASLTLTCTASGFSFSSSYYMCWLRQAPGKGLEWVACIYGGSSSSTYYASWAKGRFTISKTSSTTVTLQMTSLTAADTATYFCARDQIYDDSGFNLWGPGTLVTVSS |

Fig.1 (Cont.)

| mAB name | SEQ ID NO. | Complete k-Light chain VR sequence |
|---|---|---|
| C074 | 7 | DIVMTQTPASVEAAVGGTVTIKCQASQSISTALGWYQQKPGQRPKLLIYGASNLEFGVPSRFKGSGSGTEYTLTISDLESGDAATYYCQCSAYGSRYVGGFGGGTEVVVK |
| C031 | 8 | DVVMTQTPASVSEPVGGTVTIKCQASQSIGNALAWYQQKPGQPPKLLIYGASNLESGVSSRFRGSRSGTEFTLTISDLESADAATYYCQCSAYGSVYVGTFGGGTEVVVK |
| B106 | 9 | DVVMTQTPASVSEPVGGTVTIKCQASQSISNLLAWYQQKPGQRPKLLMSYASSLASGVSSRFKGSRSGTEYTLTISDLECADAATYYCQCTDVGSNYLGAFGGGTEVVVK |
| B100 | 10 | DIVMTQTPASVSEPVGGTVTIKCQASQGISTALAWYQQKPGQRPKLLIYSASTLASGVSSRFKGSGSGTQFTLTISDLECADAATYYCQCTAAGSVSVGAFGGGTEVVVN |
| AK57 | 11 | DPVLTQTPSSASEPVGGTVTIKCQASQSIYSYLSWYQQKPGQPPELLIYSASTLASGVPSRFKGSGSGTQFTLTISDLECADSATYYCQNNNGGSYSSAFGAFGGGTEVVVK |
| B115 | 12 | DIVMTQTPSSVSEPVGGTVTIKCQASQSISIYLSWYQQKPGQPPKRLIYKASTLESGVPSRFKGSGSGTEFTLTISDLECADAATYYCQSNYGSGSSSWEGAFGGGTEVVVK |

| mAB name | SEQ ID NO. | CDR-H1 | SEQ ID NO. | CDR-H2 | SEQ ID NO. | CDR-H3 |
|---|---|---|---|---|---|---|
| C074 | 13 | SYNMG | 19 | IISHSDNTYYASWAKG | 25 | GAAGGSGAYNL |
| C031 | 14 | NYNMA | 20 | IINAGGTAYYASWAKG | 26 | SYTSNSGAFNI |
| B106 | 15 | SYAMS | 21 | IIYSGGNAHYASWAKG | 27 | GDDSSGLRL |
| B100 | 16 | NYGVS | 22 | IISGSGFTYYASWAKG | 28 | GVVPGYNAGGL |
| AK57 | 17 | SYAMS | 23 | IIYAISDNTWFASWAKG | 29 | ALYAGYTAGYYFSL |
| B115 | 18 | SSYYMC | 24 | CIYGGSSSTYYASWAKG | 30 | DQIYDDSGFNL |

| mAB name | SEQ ID NO. | CDR-L1 | SEQ ID NO. | CDR-L2 | SEQ ID NO. | CDR-L3 |
|---|---|---|---|---|---|---|
| C074 | 31 | QASQSISTALG | 37 | GASNLEF | 43 | QCSAYGSRYVGG |
| C031 | 32 | QASQSIGNALA | 38 | GASNLES | 44 | QCSAYGSVYVGT |
| B106 | 33 | QASQSISNLLA | 39 | YASSLAS | 45 | QCTDVGSNYLGA |
| B100 | 34 | QASQGISTALA | 40 | SASTLAS | 46 | QCTAAGSVSVGA |
| AK57 | 35 | QASQSIYSYLS | 41 | SASTLAS | 47 | QNNNGGSYSSAFGA |
| B115 | 36 | QASQSISIYLS | 42 | KASTLES | 48 | QSNYGSGSSSWEGA |

Fig.1 (Cont.)

| mAB name | SEQ ID NO. | FR-H1 | SEQ ID NO. | FR-H2 | SEQ ID NO. | FR-H3 | SEQ ID NO. | FR-H4 |
|---|---|---|---|---|---|---|---|---|
| C074 | 49 | QSLEESGGRLVTPGTPLTLTCTVSGFSLS | 55 | WVRQAPGKGLEWIG | 61 | RFTISKTSTTVDLKMTSPTTEDTATYFCAR | 67 | WGQGMLVTVSS |
| C031 | 50 | QSVEESGGRLVTPGTPLTLTCTVSGFSLS | 56 | WVRQAPGEGLEYIG | 62 | RITISKTSTTVDLKISSPTAEDTATYFCAR | 68 | WGPGTLVTVSS |
| B106 | 51 | QSVEESGGRLVTPGTPLTLTCTVSGFSLS | 57 | WVRQAPGKGLEWIG | 63 | RFTISRTSTTVDLKMTSLTTEDTATYFCAR | 69 | WGQGTLVTVSS |
| B100 | 52 | QSVEESGGRLVTPGTPLTLTCTVSGFSLS | 58 | WVRQAPGKGLEYIG | 64 | RFTISKTSTTVDLKITSPTTKDTATYFCAR | 70 | WGQGTLVTVSS |
| AK57 | 53 | QSVEESGGRLVTPGTPLTLTCTVSGFSLS | 59 | WVRQAPGKGLEWIG | 65 | RFTISKTSTTVDLKITSPTTEDTATYFCAR | 71 | WGPGTLVTVSS |
| B115 | 54 | QSLEESGGDLVKPGASLTLTCTASGFSFS | 60 | WLRQAPGKGLEWVA | 66 | RFTISKTSSTTVTLQMTSLTAADTATYFCAR | 72 | WGPGTLVTVSS |

| mAB name | SEQ ID NO. | FR-L1 | SEQ ID NO. | FR-L2 | SEQ ID NO. | FR-L3 | SEQ ID NO. | FR-L4 |
|---|---|---|---|---|---|---|---|---|
| C074 | 73 | DIVMTQTPASVEAAVGGTVTIKC | 79 | WYQQKPGQRPKLLIY | 85 | GVPSRFKGSGSGTEYTLTISDLESGDAATYYC | 91 | FGGGTEVVVK |
| C031 | 74 | DVVMTQTPASVSEPVGGTVTIKC | 80 | WYQQKPGQPPKLLIY | 86 | GVSSRFRGSRSGTEFTLTISDLESADAATYYC | 92 | FGGGTEVVVK |
| B106 | 75 | DVVMTQTPASVSEPVGGTVTIKC | 81 | WYQQKPGQRPKLLMS | 87 | GVSSRFKGSRSGTEYTLTISDLECADAATYYC | 93 | FGGGTEVVVK |
| B100 | 76 | DIVMTQTPASVSEPVGGTVTIKC | 82 | WYQQKPGQRPKLLIY | 88 | GVSSRFKGSGSGTQFTLTISDLECADAATYYC | 94 | FGGGTEVVVN |
| AK57 | 77 | DPVLTQTPSSASEPVGGTVTIKC | 83 | WYQQKPGQPPELLIY | 89 | GVPSRFKGSGSGTQFTLTISDLECADSATYYC | 95 | FGGGTEVVVK |
| B115 | 78 | DIVMTQTPSSVSEPVGGTVTIKC | 84 | WYQQKPGQPPKRLIY | 90 | GVPSRFKGSGSGTEFTLTISDLECADAATYYC | 96 | FGGGTEVVVK |

Fig.1 (Cont.)

| SEQ ID NO. | Constant region sequences (CR) |
|---|---|
| 97 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 98 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 99 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |

| SEQ ID NO. | Complete Heavy-chain VR sequence |
|---|---|
| 100 | QVQLEESGGRVVQPGTSLRLSCAASGFSLSNYGVSWVRQAPGKGLEYVAIISGSGFTYYASWAKGRFTISKDTSKNTVVMQMTSLRAEDTATYFCARGVVPGYNAGGLWGQGTLVTVSS |
| 101 | EEHLEESGGRLVKPGTSLRLSCTVSGFSLSNYGVSWVRQAPGRGLEYVSIISGSGFTYYASWAKGRFTISKDTARDSVYLQMNSLRAEDTATYFCARGVVPGYNAGGLWGQGTLVTVSS |

| SEQ ID NO. | Complete Light-chain VR sequence |
|---|---|
| 102 | DIQMTQSPSSLSASVGDRITITCQASQGISTALAWYQQKPGQVPKLLIYSASTLASGVPSRFKGSGSGTEFTLTISSLQAEDVATYYCQCTAAGSVSVGAFGGGTEVVIK |
| 103 | DIVMTQSPSSVSASVGDRVTITCQASQGISTALAWYQQKPGQAPKLLIYSASTLASGVPSRFKGSGSGTDFTLTISSLQPEDSATYYCQCTAAGSVSVGAFGQGTELVIK |
| 104 | DIELTQSPSSVSASVGDRVTITCQASQGISTALAWYQQKPGQAPKLLIYSASTLASGVPSRFKGSGSGTDFTLTISSLQSEDSATYYCQCTAAGSVSVGAFGGGTKVVIE |

Fig. 2: Antibody selection through FcγRIIIa signaling assay
a)
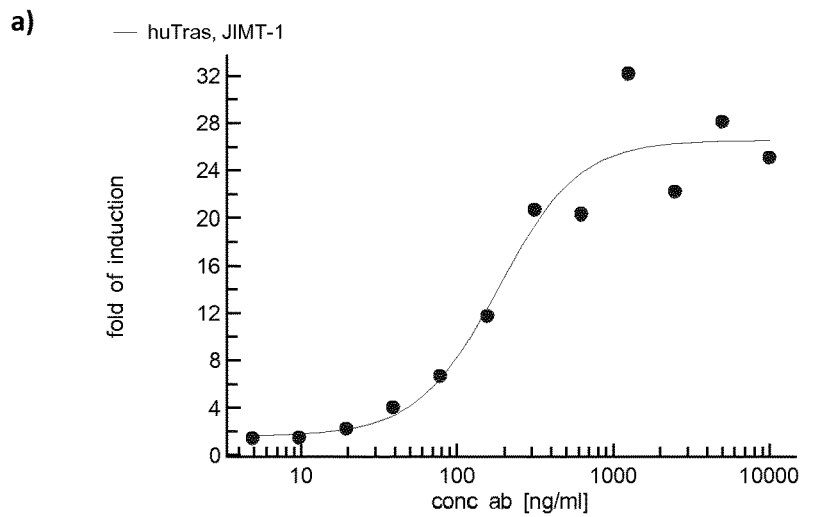
b)
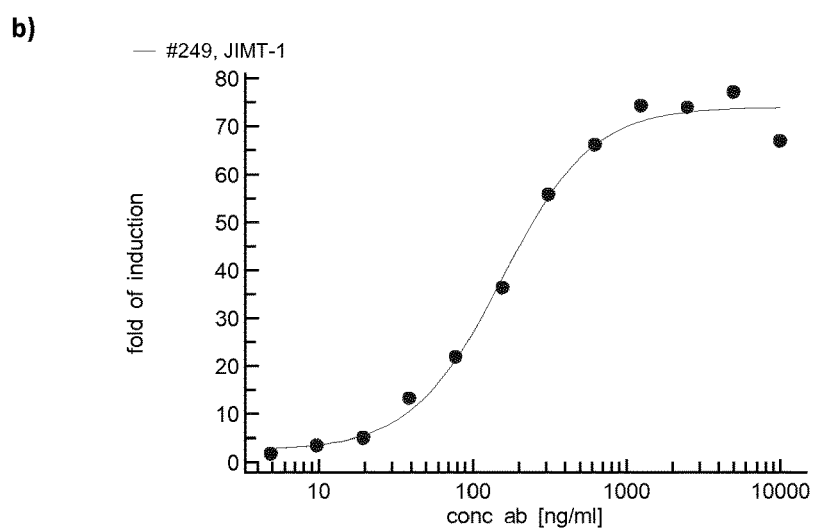
c)
| mAb | FcγRIIIa signaling (FoI) in JIMT-1 cells |
|---|---|
| AK57 | 17 |
| B115 | 70 |
| B100 | 50 |
| B106 | 50 |
| C031 | 11 |
| C074 | 22 |

Fig. 3: Epitope competition assay

| Antibody (1µg/ml) | Reference Antibody: Trastuzumab | Reference Antibody: Pertuzumab |
|---|---|---|
| Trastuzumab | +++ | - |
| Pertuzumab | - | +++ |
| AK57 | - | - |
| C031 | - | - |
| C074 | - | - |
| B100 | - | - |
| B106 | - | +++ |
| B115 | - | + |

Fig. 4: HER2 biochemical ELISA

| Antibody | EC50 (ng/mL) |
|---|---|
| MABD B100 | 5,2 |
| Trastuzumab | 3,0 |
| Pertuzumab | 4,7 |

Fig 5: Binding to SK-BR-3 cell line

| Antibody | EC50 (ng/mL) |
|---|---|
| MABD B100 | 78 |
| Trastuzumab | 153 |
| Pertuzumab | 130 |

Fig. 6: Fcγ-receptor signaling

| Antibody | EC50 (ng/mL) | F.O.I. at 10µg/mL |
|---|---|---|
| MABD B100 | 52 | 132 |
| Trastuzumab | 81 | 128 |

Fig. 7: Receptors binding in ELISA experiments
a) Binding to homologues HER receptors
| Antibody | huHER1 | huHER2 | huHER3 | huHER4 |
|---|---|---|---|---|
| MABD B100 | - | + | - | - |
| Trastuzumab | - | + | - | - |
| Pertuzumab | - | + | - | - |
| MAB-16-0160 | - | + | - | - |
| MAB-16-0161 | - | + | - | - |
| MAB-16-0163 | - | + | - | - |
| MAB-16-0165 | - | + | - | - |
b) Binding to orthologues of HER2
| Antibody | huHER2 | cyHER2 | muHER2 | rtHER2 |
|---|---|---|---|---|
| MABD B100 | + | + | - | (+) |
| Trastuzumab | + | + | - | (+) |
| Pertuzumab | + | + | - | (+) |
| MAB-16-0160 | + | + | - | (+) |
| MAB-16-0161 | + | + | - | (+) |
| MAB-16-0163 | + | + | - | (+) |
| MAB-16-0165 | + | + | - | (+) |
Fig. 8: Apoptosis induction on SK-BR-3 cell line
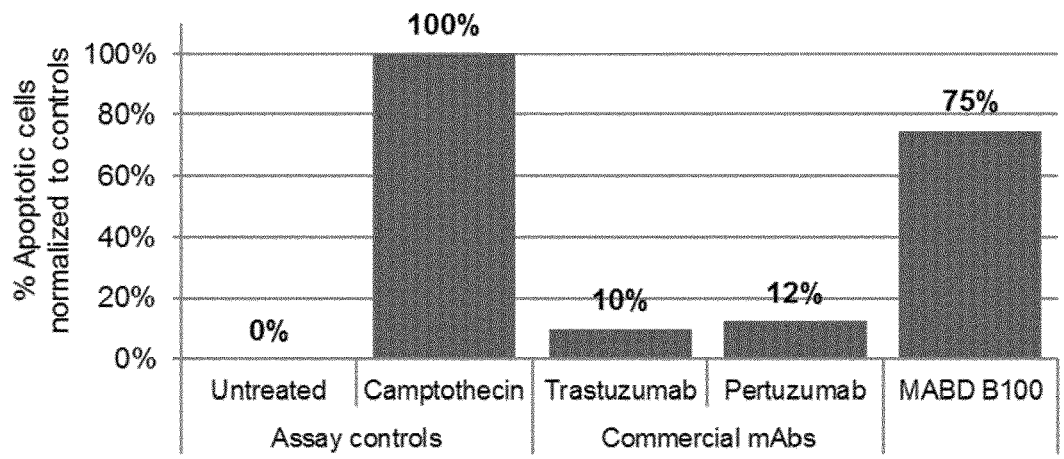

Fig. 9: HER2 biochemical ELISA of humanized Mab variants

| Antibody | Version | EC50 (ng/mL) |
|---|---|---|
| MABD B100 | Chimeric | 5,2 |
| MAB-16-0160 | Humanized 1 | 5,3 |
| MAB-16-0161 | Humanized 2 | 9,2 |
| MAB-16-0163 | Humanized 3 | 6,0 |
| MAB-16-0165 | Humanized 4 | 7,5 |

Fig 10: Binding to SK-BR-3 cell line of humanized Mab variants

| Antibody | Version | EC50 (ng/mL) |
|---|---|---|
| MABD B100 | Chimeric | 78 |
| MAB-16-0160 | Humanized 1 | 42 |
| MAB-16-0161 | Humanized 2 | 19 |
| MAB-16-0163 | Humanized 3 | 71 |
| MAB-16-0165 | Humanized 4 | 76 |

Fig 11: Fcγ-receptor signaling of humanized Mab variants

| Antibody | Version | EC50 (ng/mL) |
|---|---|---|
| MABD B100 | Chimeric | 254 |
| MAB-16-0160 | Humanized 1 | 274 |
| MAB-16-0161 | Humanized 2 | 172 |
| MAB-16-0163 | Humanized 3 | 94 |
| MAB-16-0165 | Humanized 4 | 59 |

Fig.12: Apoptosis induction of humanized Mab variants
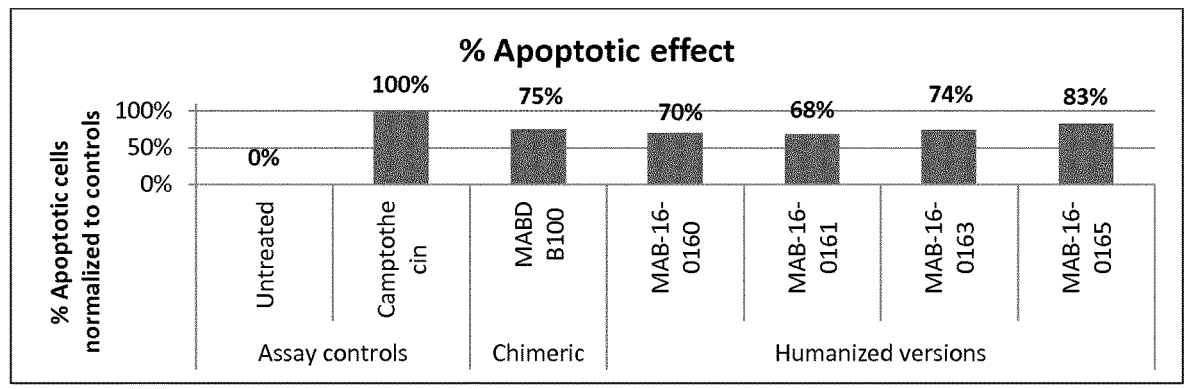
Fig. 13: *In vivo* Profile of MABD B100: Tumor burden after treatment
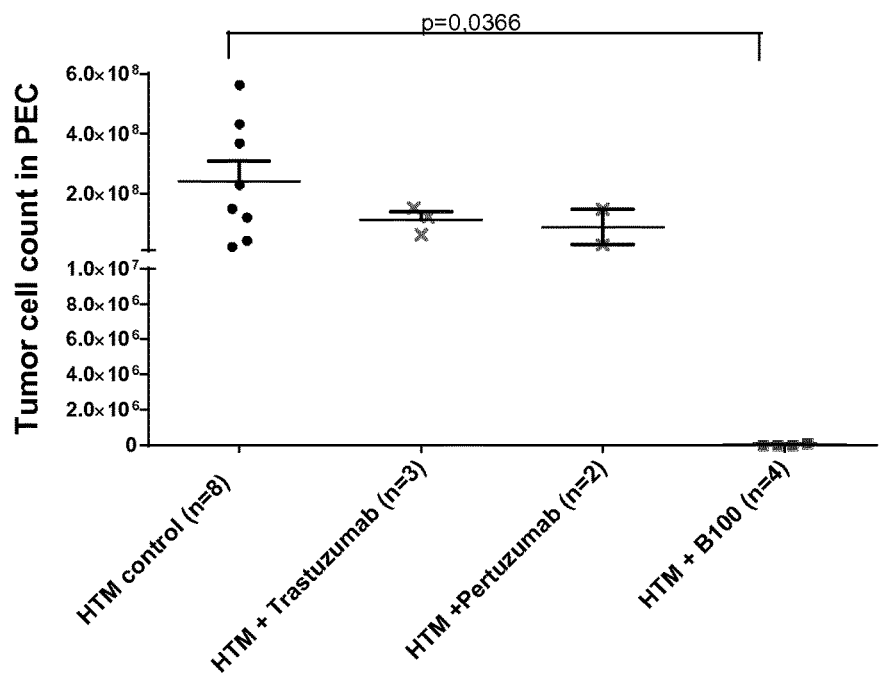

Fig. 14: *In vivo* profile of MABD B100: Anti-tumor and anti-metastatic activity a) HER2+ Tumor cells in histological sections

|  | HTM control (MAB Study) | HTM trast (MAB Study) | HTM + B100 (MAB Study) | HTM+ Pert (MAB Study) | HTM Control (Wege et al. 2016) | HTM trast (Wege et al. 2016) |
|---|---|---|---|---|---|---|
| Lung | 3/3 | Not done | 1/1 | 1/2 | 13/14 | 8/8 |
| Liver | 5/5 | 3/3 | 0/3 | 1/2 | 7/12 | 7/8 |
| Brain | 7/7 | 3/3 | 0/4 | 1/2 | 5/5 | 0/3 | b) HER2 + tumor cells analyzed by flow cytometry

|  | HTM control (MAB Study) | HTM trast (MAB Study) | HTM + B100 (MAB Study) | HTM+ Pert (MAB Study) | HTM control (Wege et al. 2016) | HTM + Trast (Wege et al. 2016) |
|---|---|---|---|---|---|---|
| Lung | 7/7 | 3/3 | 1/3 | 2/2 | 9/10 | 8/8 |
| Bm | 3/7 | 3/3 | 0/4 | 1/2 | 7/11 | 6/11 |

Fig. 15: *In vivo* profile of MABD B100: Dissemination of tumor cells to bone marrow

|  | HTM |
|---|---|
| Control mice (MAB Stuy) | 6/8 (75 %) |
| B100 | 0/4 (0%) |
| Trastuzumab (MAB Study) | 3/3 (100%) |
| Pertuzumab (MAB Study) | 1/2 (50%) |
| Control mice (Wege et al. 2016) | 12/20 (60%) |
| Trastuzumab (Wege et al. 2016) | 10/14 (71%) |

HER-2 BINDING ANTIBODIES

CROSS REFERENCE TO RELATED APPLICATIONS

This application claims the priority benefit of PCT/EP2017/060935 filed on May 8, 2017 which claims priority benefit of European Application No. 16168619.1 filed May 6, 2016. The entire contents of which are hereby incorporated by reference herein.

FIELD OF INVENTION

The present invention relates to monoclonal antibodies that specifically bind to HER2, or a fragment or derivative thereof or a polypeptide that contains at least a portion of said antibody that is sufficient to confer specific HER2 binding to the polypeptide. The invention also relates to methods of using said antibodies and compositions comprising them in the diagnosis, prognosis and therapy of diseases such as cancer, autoimmune diseases, inflammatory disorders, and infectious diseases.

SEQUENCE LISTING

The instant application contains a Sequence Listing which has been submitted electronically in ASCII format and is hereby incorporated by reference in its entirety. Said ASCII copy, created on Oct. 25, 2018, is named 18744_0121_SL.txt and is 47,653 bytes in size.

BACKGROUND

Receptor tyrosine-protein kinase erbB-2, also known as CD340 (cluster of differentiation 340), proto-oncogene Neu, Erbb2 (rodent), or ERBB2 (human) is a protein that in humans is encoded by the ERBB2 gene, which is also frequently called HER2 (from human epidermal growth factor receptor 2) or HER2/neu.

HER2 is a member of the human epidermal growth factor receptor (HER/EGFR/ERBB) family. HER2, a known proto-oncogene, is located at the long arm of human chromosome 17 (17q12). Amplification or overexpression of this oncogene has been shown to play an important role in the development and progression of certain aggressive types of breast cancer. In recent years, the protein has become an important biomarker and target of therapy for approximately 30% of breast cancer patients.

The ErbB family consists of four plasma membrane-bound receptor tyrosine kinases. One of which is erbB-2, and the other members being epidermal growth factor receptor, erbB-3 (neuregulin-binding; lacks kinase domain), and erbB-4. All four contain an extracellular ligand binding domain, a transmembrane domain, and an intracellular domain that can interact with a multitude of signaling molecules and exhibit both ligand-dependent and ligand-independent activity. HER2 can heterodimerise with any of the other three receptors and is considered to be the preferred dimerisation partner of the other ErbB receptors.

Dimerisation results in the autophosphorylation of tyrosine residues within the cytoplasmic domain of the receptors and initiates a variety of signaling pathways. These include the mitogen-activated protein kinase (MAPK) pathway, the phosphoinositide 3-kinase (PI3K/Akt) pathway, phospholipase Cγ-, protein kinase C (PKC)-, and the Signal transducer and activator of transcription (STAT) pathways. Therefore, signaling through the ErbB family of receptors promotes cell proliferation and opposes apoptosis, and consequently must be tightly regulated to prevent uncontrolled cell growth from occurring.

Amplification or over-expression of the ERBB2 gene occurs in approximately 15-30% of breast cancers. It is strongly associated with increased disease recurrence and a poor prognosis. Over-expression is also known to occur in ovarian, stomach, and aggressive forms of uterine cancer, such as uterine serous endometrial carcinoma. For example, HER-2 is overexpressed in approximately 7-34% of patients with gastric cancer and in 30% of salivary duct carcinomas.

Diverse structural alterations have been identified that cause ligand-independent firing of this receptor, doing so in the absence of receptor over-expression.

HER2 is found in a variety of tumors and some of these tumors carry point mutations in the sequence specifying the transmembrane domain of HER2. Substitution of a valine for a glutamic acid in the transmembrane domain can result in the constitutive dimerization of this protein in the absence of a ligand. HER2 mutations have also been found in non-small-cell lung cancers (NSCLC) and can direct treatment.

HER2 is the target of the monoclonal antibody trastuzumab (marketed as Herceptin). Trastuzumab is effective only in cancers where HER2 is over-expressed. One year of trastuzumab therapy is recommended for all patients with HER2-positive breast cancer who are also receiving chemotherapy. An important downstream effect of trastuzumab binding to HER2 is an increase in p27, a protein that halts cell proliferation.

Another monoclonal antibody, pertuzumab, which inhibits dimerization of HER2 and HER3 receptors, was approved by the FDA for use in combination with trastuzumab in June 2012. Additionally, NeuVax (Galena Biopharma) is a peptide-based immunotherapy that directs "killer" T cells to target and destroy cancer cells that express HER2. It has entered phase 3 clinical trials.

HER2 testing is performed in breast cancer patients to assess prognosis and to determine suitability for trastuzumab therapy. It is important that trastuzumab is restricted to HER2-positive individuals as it is expensive and has been associated with cardiac toxicity. For HER2-negative tumors, the risks of trastuzumab clearly outweigh the benefits.

Thus, there is a need for the development of novel, more effective antibodies that can be used in follow-up therapies when results of the gold-standard therapy with trastuzumab (and chemotherapy) are not satisfying or as an alternative in combination with existing antibodies.

Aim of the study underlying the present invention was to generate a large quantity of high-affinity antibodies against HER2 in order to find new molecules with a novel mechanism of action in comparison to existing antibodies and therapies, such as trastuzumab and pertuzumab.

SUMMARY OF INVENTION

The present invention relates to a monoclonal antibody that specifically binds to HER2, or a fragment or derivative thereof or a polypeptide that contains at least a portion of said antibody that is sufficient to confer specific HER2 binding to the polypeptide, wherein said antibody binds to the human Fc receptor and induces FcR mediated signaling pathways.

In some embodiments, the antibody according to the invention binds to a different epitope as trastuzumab.

The invention also relates to a method of treating an HER-2 mediated disease in a patient, comprising administering to a patient a pharmaceutically effective amount of the antibody according to the invention.

The present invention further relates to a pharmaceutical composition comprising a pharmaceutically acceptable carrier and a therapeutically effective amount of the antibody according to the invention. Said pharmaceutical composition can be administered to a patient in a method of treating an HER-2 mediated disease according to the invention.

Definitions

The term "rabbit" according to the invention means an animal of the members of the taxonomic order Lagomorpha, which includes the families (hares and rabbits) and Ochotonidae (pikas), preferably of genus *Oryctolagus*.

The term "antibody" encompasses the various forms of antibody structures including, but not being limited to, whole antibodies and antibody fragments as long as it shows the properties according to the invention.

The term "rabbit monoclonal antibody" according to the invention means a monoclonal antibody produced by immunizing a rabbit and isolated from an antigen producing cell of said rabbit as well as such an antibody which is further modified, preferably a humanized antibody, a chimeric antibody, a fragment thereof, or a further genetically engineered and recombinant produced antibody as long as the characteristic properties according to the invention are retained. Preferably the antibody is from a B cell or a rabbit hybridoma cell of said rabbit.

The term "antibody producing cell" according to the invention means a rabbit B cell which produce antibodies, preferably a B cell or rabbit hybridoma cell.

"Native antibodies" are usually heterotetrameric glycoproteins composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

The terms "Fc receptor" or "FcR" as used here refers to a human receptor that binds to the Fc region of an antibody. FcRs bind IgG antibodies and include receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, Annu. Rev. Immunol. 15:203-234 (1997)). FcRIIIA (CD16a) mediates ADCC. FcRs are reviewed in Ravetch and Kinet, Annu. Rev. Immunol 9:457-92 (1991); Capel et al, Immunomethods 4:25-34 (1994); and de Haas et al, J. Lab. CHn. Med. 126:330-41 (1995). These and all other FcRs are encompassed by the term "FcR" herein. The term also includes the neonatal receptor, FcRn, which is responsible for the transfer of maternal IgGs to the fetus (Guyer et al, J. Immunol. 117:587 (1976) and Kim et al, J. Immunol. 24:249 (1994)) and mediates slower catabolism, thus longer half-life.

The "constant domains (constant parts)" are not involved directly in binding of an antibody to an antigen, but exhibit e.g. also effector functions. The heavy chain constant region that corresponds to human IgG1 is called γ1 chain. The heavy chain constant region that correspond to human IgG3 is called γ3 chain. Human constant γ heavy chains are described in detail by Kabat, E. A. et al., Sequences of Proteins of Immunological Interest, 5th ed., Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527. Constant domains of IgG1 or IgG3 type are glycosylated at Asn297. "Asn 297" according to the invention means amino acid asparagine located at about position 297 in the Fc region; based on minor sequence variations of antibodies, Asn297 can also be located some amino acids (usually not more than +3 amino acids) upstream or downstream.

The term "antibody effector function(s)," or "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Typical effector functions are ADCC, ADCP and CDC. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FCYRIII. FCR expression on hematopoietic cells is summarized in Table 3 on page 464 of Ravetch, and Kinet, Annu. Rev. Immunol 9 (1991) 457-492. The term "Antibody-dependent cellular phagocytosis" and "ADCP" refer to a process by which antibody-coated cells are internalized, either in whole or in part, by phagocytic immune cells (e.g., macrophages, neutrophils and dendritic cells) that bind to an immunoglobulin Fc region.

C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_5$, and $IgA_2$. The heavy chain constant domains that correspond to the different classes of immunoglobulins are called a, δ, ε, γ, and μ, respectively.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions.

Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, Md. (1991).

A "variant Fc region" comprises an amino acid sequence which differs from that of a "native" or "wildtype" sequence Fc region by virtue of at least one "amino acid modification" as herein defined.

The term "Fc-variant" as used herein refers to a polypeptide comprising a modification in the Fc domain. For all positions discussed in the present invention, numbering is according to the EU index. The EU index or EU index as in Kabat or EU numbering scheme refers to the numbering of the EU antibody (Edelman, et al., Proc Natl Acad Sci USA 63 (1969) 78-85, hereby entirely incorporated by reference.) The modification can be an addition, deletion, or substitution. Substitutions can include naturally occurring amino acids and non-naturally occurring amino acids. Variants may comprise non-natural amino acids.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. A FcR which binds an IgG antibody (a gamma receptor) includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see review in Daeron, M., Annu. Rev. Immunol. 15 (1997) 203-234). FcRs are reviewed in Ravetch, and Kinet, Annu. Rev. Immunol 9 (1991) 457-492; Capel, et al., Immunomethods 4 (1994) 25-34; and de Haas, et al., J. Lab. Clin. Med. 126 (1995) 330-41. Other FcRs, including those to be identified in the future, are encompassed by the term "FcR" herein. The term also includes the neonatal receptor, FcRn, which is responsible for the transfer of maternal IgGs to the fetus (Guyer, et al., J. Immunol. 117 (1976) 587 and Kim, et al., J. Immunol. 24 (1994) 249).

By "IgG Fc ligand" as used herein is meant a molecule, preferably a polypeptide, from any organism that binds to the Fc region of an IgG antibody to form an Fc/Fc ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis, et al., Immunological Reviews 190 (2002) 123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIA, FcγRIB, and FcγRIC; FcγRII (CD32), including isoforms FcγRIIA (including allotypes H131 and R131), FcγRIIB (including FcγRIIB-1 and FcγRIIB-2), and FcγRIIc; and FcγRIII (CD 16), including isoforms FcγRIIIA (including allotypes VI 58 and F158) and FcγRIIIb (including allotypes FcγRIIB-NA1 and FcγRIIB-NA2) (Jefferis, et al., Immunol Lett 82(2002) 57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD 16), and FCYRIII-2 (CD 16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

An "immunoconjugate" means an antibody conjugated to one or more cytotoxic agents, such as a chemotherapeutic agent, a drug, a growth inhibitory agent, a toxin, another antibody or a radioactive isotope.

"Antibody fragments" comprise a portion of a full-length antibody, preferably the variable regions thereof, or at least the antigen binding site thereof. Examples of antibody fragments include diabodies, Fab fragments, and single-chain antibody molecules. scFv antibodies are, e.g., described in Huston, J. S., Methods in Enzymol. 203 (1991) 46-88.

The terms "monoclonal antibody" or "monoclonal antibody composition" as used herein refer to a preparation of antibody molecules of a single amino acid composition.

The term "humanized antibody" or "humanized version of an antibody" refers to antibodies for which both heavy and light chains are humanized as a result of antibody engineering. A humanized chain is typically a chain in which the V-region amino acid sequence has been changed so that, analyzed as a whole, is closer in homology to a human germline sequence than to the germline sequence of the species of origin. Humanization assessment is based on the resulting amino acid sequence and not on the methodology per se.

The terms "specifically binding, against target, or anti-target antibody", as used herein, refer to binding of the antibody to the respective antigen (target) or antigen-expressing cell, measured by ELISA, wherein said ELISA preferably comprises coating the respective antigen to a solid support, adding said antibody under conditions to allow the formation of an immune complex with the respective antigen or protein, detecting said immune complex by measuring the Optical Density values (OD) using a secondary antibody binding to an antibody according to the invention and using a peroxidase-mediated color development.

The term "antigen" according to the invention refers to the antigen used for immunization or a protein comprising said antigen as part of its protein sequence. For example, for immunization a fragment of the extracellular domain of a protein (e.g. the first 20 amino acids) can be used and for detection/assay and the like the extracellular domain of the protein or the full length protein can be used.

The term "specifically binding" or "specifically recognized" herein means that an antibody exhibits appreciable affinity for an antigen and, preferably, does not exhibit significant cross-reactivity.

"Appreciable" binding affinity includes binding with an affinity of at least $10^{-7}$M, specifically at least $10^{-8}$M, more specifically at least $10^{-9}$M, or even yet more specifically at least $10^{-10}$M.

An antibody that "does not exhibit significant cross-reactivity" is one that will not appreciably bind to an undesirable other protein. Specific binding can be determined according to any art-recognized means for determining such binding, e.g. by competitive binding assays such as ELISA.

All protein terms as used herein refers to the human proteins. If a protein from another species is meant, this is explicitly mentioned.

The "variable region (or domain) of an antibody according to the invention" (variable region of a light chain (VL), variable region of a heavy chain (VH)) as used herein denotes each of the pair of light and heavy chain regions which are involved directly in binding the antibody to the antigen. The variable light and heavy chain regions have the same general structure and each region comprises four framework (FR) regions whose sequences are widely conserved, connected by three complementary determining regions, CDRs.

The term "antigen-binding portion of an antibody" when used herein refer to the amino acid residues of an antibody which are responsible for antigen-binding. The antigen-binding portion of an antibody comprises preferably amino acid residues from the "complementary determining regions" or "CDRs". The CDR sequences are defined according to Kabat et al, Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable region. For example, a heavy chain variable region may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "cancer" as used herein may be, for example, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, colon cancer, lung cancer, or pancreatic cancer.

DETAILED DESCRIPTION OF INVENTION

The present invention originates from making use of the technologies established by the inventors, which allow for the production of a large amount of diverse molecules with different properties.

The inventors produced more than 40.000 supernatants of B-cells and tested them, out of which they identified more than 7.500 antibodies, which bind to HER-receptors mono- or oligospecific in ELISA assays.

The RNA and amino acid sequences of 564 molecules were determined, and respective antibodies were cloned, expressed and purified, generating about 300 recombinant chimeric antibodies. This genetic modification and purification of the antibodies allows for specific biochemical testing of defined amounts of antibody, thus appropriate quantitative evaluation and for consequently for in vivo use as unwanted immune defense reactions are minimized.

The recombinant monoclonal antibodies were tested and compared in vitro and in vivo. Surprisingly, several molecules were found that show at least a 2-fold increase of FcγRIIIa mediated activity in JIMT-1 cells, i.e. a higher activation of the NFAT pathway than trastuzumab/Herceptin. Moreover, some of the antibodies were found to bind to different epitopes than the gold-standard antibodies, trastuzumab (TZ) and pertuzumab (PZ), for breast cancer therapy.

Therefore, the present invention relates to a monoclonal antibody that specifically binds to HER2, or a fragment or derivative thereof or a polypeptide that contains at least a portion of said antibody that is sufficient to confer specific HER2 binding to the polypeptide, comprising:
- a) a heavy chain variable region (VH) comprising CDR-H1, CDR-H2, and CDR-H3,
  - wherein the CDR-H1 region comprises an amino acid sequence selected from the group of SEQ ID NO: 13-18,
  - wherein the CDR-H2 region comprises an amino acid sequence selected from the group of SEQ ID NO: 19-24,
  - and wherein the CDR-H3 region comprises an amino acid sequence selected from the group of SEQ ID NO: 25-30; and
- b) a light chain variable region (VL) comprising CDR-L1, CDR-L2, CDR-L3, and
  - wherein the CDR-L1 region comprises an amino acid sequence selected from the group of SEQ ID NO: 31-36,
  - wherein the CDR-L2 region comprises an amino acid sequence selected from the group of SEQ ID NO: 37-42,
  - and wherein the CDR-L3 region comprises an amino acid sequence selected from the group of SEQ ID NO: 43-48.

Furthermore, the antibody according to the invention may comprise a
- a) heavy chain variable region (VH) that comprises the framework regions FR-H1, FR-H2, FR-H3, and FR-H4,
  - wherein FR-H1 region comprises an amino acid sequence selected from the group of SEQ ID NO: 49-54,
  - wherein the FR-H2 region comprises an amino acid sequence selected from the group of SEQ ID NO: 55-60,
  - wherein the FR-H3 region comprises an amino acid sequence selected from the group of SEQ ID NO: 61-66; and
  - and wherein the FR-H4 region comprises an amino acid sequence selected from the group of SEQ ID NO: 67-72;
- b) light chain variable region (VL) that comprises the framework regions FR-L1, FR-L2, FR-L3, and FR-L4,
  - wherein the FR-L1 region comprises an amino acid sequence selected from the group of SEQ ID NO: 73-78,
  - wherein the FR-L2 region comprises an amino acid sequence selected from the group of SEQ ID NO: 79-84,
  - and wherein the FR-L3 region comprises an amino acid sequence selected from the group of SEQ ID NO: 85-90 and
  - wherein the FR-L4 region comprises an amino acid sequence selected from the group of SEQ ID NO: 91-96.

In one embodiment, the antibody according to the invention is a monoclonal IgG antibody. Preferably, the antibody according to the invention is a monoclonal IgG1 antibody.

The monoclonal antibody according to the invention is an antibody that specifically binds to HER2, or a fragment or derivative thereof or a polypeptide that contains at least a portion of said antibody that is sufficient to confer HER2 binding specificity, comprising a heavy chain variable (VH) region is at least 90% identical to a VH region selected from the group consisting of VH regions of SEQ ID NO: 1 to 6 and SEQ ID NO: 100 to 101, and a light chain variable (VL) region that is at least 90% identical to a VL region selected from the group consisting of VL regions of SEQ ID NO: 7 to 12 and SEQ ID NO 102 to 104.

In an antibody according to the invention, the heavy chain variable (VH) region can be at least 60% identical, preferably at least 70% identical, more preferably at least 80% identical to a VH region selected from the group consisting of VH regions of SEQ ID NO: 1 to 6 and SEQ ID NO: 100 to 101.

In one embodiment, the antibody according to the invention comprises a heavy chain variable region (VH) sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an amino acid sequence selected from the group of VH sequences according to the invention, i.e. SEQ ID NO: 1 to 6 and SEQ ID NO: 100 to 101.

Preferably, the antibody comprises a heavy chain variable (VH) region that is at least 90% identical to the VH region of SEQ ID NO: 4, preferably the VH region is 91%, 92%, 93%, 94%, 95%, 96%, 97%, 98%, 99%, or 100% identical to SEQ ID NO: 4, and most preferred the VH region comprises SEQ ID NO: 4.

In certain embodiments, a VH sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically according to the invention to the respective antigen. In certain embodiments, a total of 1 to 10 amino acids have been substituted, inserted and/or deleted in each of said VH sequences. In certain embodiments, substitutions, insertions, or deletions occur in regions outside the CDRs (i.e., in the FRs).

In a preferred embodiment, the heavy chain variable region (VH) sequence is selected from the group consisting of VH regions of SEQ ID NO: 1 to 6 and SEQ ID NO: 100 to 101.

Even more preferred, the heavy chain variable region (VH) sequence is SEQ ID NO:1, SEQ ID NO:2, SEQ ID NO:3, SEQ ID NO:4, SEQ ID NO:5, SEQ ID NO:6, SEQ ID NO: 100 or 101. Most preferred, the VH sequence is SEQ ID NO:4.

In an antibody according to the invention, the light chain variable (VL) region can be at least 60% identical, preferably at least 70% identical, more preferably at least 80% identical to a VL region selected from the group consisting of VL regions of SEQ ID NO: 7 to 12 and SEQ ID NO 102 to 104.

In one embodiment, the antibody according to the invention comprises a light chain variable region (VL) having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the amino acid sequence of the VL sequences according to the invention.

Preferably, the antibody comprises a light chain variable (VL) region that is at least 90% identical to the VL region of SEQ ID NO: 10, preferably 91%, 92%, 93%, 94%, 95%, 96%, 97%, 98%, 99%, or 100% identical, and most preferred the VL region comprises SEQ ID NO: 10.

In some embodiments, a VL sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically to the respective antigen. In certain embodiments, a total of 1 to 10 amino acids have been substituted, inserted and/or deleted in said VL sequences. In certain embodiments, the substitutions, insertions, or deletions occur in regions outside the CDRs (i.e., in the FRs).

In a preferred embodiment, the light chain variable region (VL) sequence is selected from the group consisting of VL regions of SEQ ID NO: 7 to 12 and SEQ ID NO 102 to 104.

Even more preferred, the heavy chain variable region (VL) sequence is SEQ ID NO:7, SEQ ID NO:8, SEQ ID NO:9, SEQ ID NO:10, SEQ ID NO:11, SEQ ID NO:12, SEQ ID NO 102, SEQ ID NO 103 or 104.

Most preferred, the VL sequence is SEQ ID NO:10.

Further preferred is that the VL sequences according to the invention comprise a mutation at position 90. Preferably, the VL sequences comprising a sequence from the group of SEQ ID NO: 10, 102, 103 and 104, comprise a mutation at position 90. Preferably the mutation is a Cysteine to Serine mutation. However, it can also be a different amino acid substitution. The VL sequences may of course also comprise further mutations as detailed above.

The invention also relates to an antibody, wherein its VH region is at least 90% identical to a VH region of SEQ ID NO: 1+n and its VL region is at least 90% identical to a VL region of SEQ ID NO: 7+n, wherein n is a number selected from the group consisting of 0 to 5.

The present invention also relates to an antibody, wherein the antibody comprises a VH region selected from the group consisting of VH regions of SEQ ID NO: 1+n and its VL region is selected from the group consisting of VL regions of SEQ ID NO: 7+n, wherein n is a number selected from the group consisting of 0 to 5.

The present invention also relates to an antibody, wherein the antibody comprises a VH region selected from the group of VH regions comprising a CDR-H1 region of SEQ ID NO: 13+n, a CDR-H2 region of SEQ ID NO: 19+n and a CDR-H3 region of SEQ ID NO: 25+n, wherein n is a number selected from the group consisting of 0 to 5.

Furthermore, an antibody according to the invention may comprise a VL region selected from the group of VL regions comprising a CDR-L1 region of SEQ ID NO: 31+n, a CDR-L2 region of SEQ ID NO: 37+n and a CDR-L3 region of SEQ ID NO: 43+n, wherein n is a number selected from the group consisting of 0 to 5.

An antibody according to the invention may also comprise a VH region selected from the group of VH regions comprising a CDR-H1 region of SEQ ID NO: 13+n, a CDR-H2 region of SEQ ID NO: 19+n and a CDR-H3 region of SEQ ID NO: 25+n, and in that the antibody comprises a VL region selected from the group of VL regions comprising a CDR-L1 region of SEQ ID NO: 31+n, a CDR-L2 region of SEQ ID NO: 37+n and a CDR-L3 region of SEQ ID NO: 43+n, wherein n is a number selected from the group consisting of 0 to 5.

"n is a number selected from the group of 0 to 5" according to the invention means a number selected from the group of 0, 1, 2, 3, 4, and 5. The number "n" according to the invention is meant to be identical for the same antibody, its heavy and light chains, its variable regions and CDR regions.

Moreover, an antibody according to the present invention may comprise a VH region and a VL region comprising the respective CDR1, CDR2 and CDR3 regions and the respective FR1, FR2, FR3, and FR4 regions of an antibody selected from the group consisting of C074, C031, B106, B100, AK57, B115.

Preferably, the antibody comprises the VH region and VL region comprising the respective CDR1, CDR2 and CDR3 regions and the respective FR1, FR2, FR3, and FR4 regions of the antibody designated as B100 (corresponding to MABD B100).

Preferably B100 is a humanized antibody.

Preferably, an antibody according to the invention comprises SEQ ID NO.: 1 and 7. In another embodiment, an antibody according to the invention comprises SEQ ID NO.: 2 and 8. An antibody according to the invention may also comprise SEQ ID NO.: 3 and 9 or SEQ ID NO.: 4 and 10, or SEQ ID NO.: 5 and 11, or SEQ ID NO.: 6 and 12.

In a further preferred embodiment according to the invention, the antibody comprises SEQ ID NO.: 1, 7, and 98. In another embodiment, the antibody according to the invention comprises SEQ ID NO.: 2, 8, and 98. An antibody according to the invention may also comprise SEQ ID NO.: 3, 9, and 98, or SEQ ID NO.: 4, 10, and 98, or SEQ ID NO.: 5, 11, and 99 or SEQ ID NO.: 6, 12, and 98.

In a further preferred embodiment according to the invention, the antibody comprises SEQ ID NO.: 1,7, and 97. In another embodiment, the antibody according to the invention comprises SEQ ID NO.: 2, 8, and 97. An antibody according to the invention may also comprise SEQ ID NO.: 3, 9, and 97, or SEQ ID NO.: 4, 10, and 97, or SEQ ID NO.: 5, 11, and 97 or SEQ ID NO.: 6, 12, and 97.

In a further preferred embodiment according to the invention, the antibody comprises SEQ ID NO.: 1, 7, 97 and 98. In another embodiment, the antibody according to the invention comprises SEQ ID NO.: 2, 8, 97 and 98. An antibody according to the invention may also comprise SEQ ID NO.: 3, 9, 97 and 98, or SEQ ID NO.: 4, 10, 97 and 98, or SEQ ID NO.: 5, 11, 97 and 99 or SEQ ID NO.: 6, 12, 97 and 98.

The present invention also relates to a monoclonal antibody that specifically binds to HER2, or a fragment or derivative thereof or a polypeptide that contains at least a portion of said antibody that is sufficient to confer HER2 binding specificity, comprising:

a) a heavy chain variable region (VH) comprising FR-H1, CDR-H1, FR-H2, CDR-H2, FR-H3, CDR-H3 and FR-H4
    wherein the CDR-H1 region comprises an amino acid sequence according to the formula:

$(S/N)_1\text{-}(Y/S)_2\text{-}(N/A/G/Y)_3\text{-}(M/V/Y)_4\text{-}(G/A/S/M)_5\text{-}(O/C)_6$ wherein the CDR-H2 region comprises an amino acid sequence according to the formula:

$(I/C)_1\text{-}(I)_2\text{-}(N/S/Y)_3\text{-}(H/A/S/G)_4\text{-}(G/I/S)_5\text{-}(D/G/S)_6\text{-}(N/T/F/D/S)_7\text{-}(T/A/N/S)_8\text{-}(Y/H/T/S)_9\text{-}(T/Y/W)_{10}\text{-}(F/A/Y)_{11}\text{-}(S/A/Y)_{12}\text{-}(W/A/S)_{13}\text{-}(W/A/S)_{14}\text{-}(K/A/W)_{15}\text{-}(G/A/K)_{16}\text{-}(0/G/K)_{17}\text{-}(0/AG)_{18}$ and wherein the CDR-H3 region comprises an amino acid sequence according to the formula:

$(G/S/A/D)_1\text{-}(A/Y/D/V/L/Q)_2\text{-}(A/T/D/V/Y/I)_3\text{-}(P/A/S/G/Y)_4\text{-}(G/N/S/D)_5\text{-}(D/G/S/Y)_6\text{-}(G/T/N/L/S)_7\text{-}(R/A/G)_8\text{-}(Y/F/L/G)_9\text{-}(0/N/G/Y)_{10}\text{-}(0/I/Y/L)_{11}\text{-}(0/F)_{12}\text{-}(0/S)_{13}\text{-}(0/L)_{14}$ b) a light chain variable region (VL) comprising FR-L1, CDR-L1, FR-L2, CDR-L2, FR-L3, CDR-L3, and FR-L4
    wherein the CDR-L1 region comprises an amino acid sequence according to the formula:

$(Q_1\text{-}(A)_2\text{-}(S)_3\text{-}(Q)_4\text{-}(S)_5\text{-}(I)_6\text{-}(G/S/Y)_7\text{-}(T/N/S/I)_8\text{-}(Y/A/L)_9\text{-}(L)_{10}\text{-}(G/A/S)_{11}$ wherein the CDR-L2 region comprises an amino acid sequence according to the formula:

$(G/Y/S/K)_1\text{-}(A)_2\text{-}(S)_3\text{-}(N/S/T)_4\text{-}(L)_5\text{-}(E/A)_6\text{-}(F/S)_7$ and wherein the CDR-L3 region comprises an amino acid sequence according to the formula:

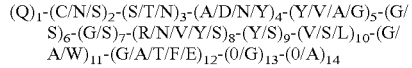

"0" herein indicates that there does not have to be an amino acid at this position.

In one preferred embodiment, the antibody of the invention comprises a serine at position 2 of CDR-L3.

Most preferred, an antibody according to the invention comprises a CDR-H1 region comprising SEQ ID NO 16, a CDR-H2 region comprising SEQ ID NO: 22, a CDR-H3 region comprising SEQ ID NO: 28, and a CDR-L1 region comprising SEQ ID NO: 34. a CDR-L2 region comprising SEQ ID NO: 40, and a CDR-L3 region comprising SEQ ID NO: 46.

A monoclonal antibody according to the invention can be rabbit antibody. In a preferred embodiment, the antibody of the invention is a rabbit/human chimeric antibody. In a further preferred version, the antibody is a humanized antibody.

Therefore, in a preferred embodiment, an antibody according to the invention is a humanized antibody comprising a heavy chain variable region (VH) comprising FR-H1, CDR-H1, FR-H2, CDR-H2, FR-H3, CDR-H3 and FR-H4 or a fragment or derivative thereof or a polypeptide that contains at least a portion of said antibody that is sufficient to confer HER2 binding specificity, comprising:

a) a heavy chain variable region (VH) comprising FR-H1, CDR-H1, FR-H2, CDR-H2, FR-H3, CDR-H3 and FR-H4
    wherein the CDR-H1 region comprises an amino acid sequence according to the formula:

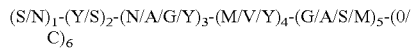

wherein the CDR-H2 region comprises an amino acid sequence according to the formula:

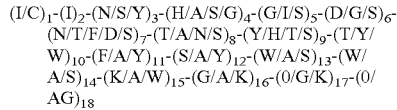

and wherein the CDR-H3 region comprises an amino acid sequence according to the formula:

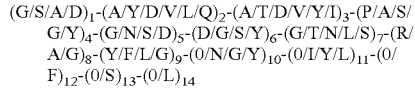

b) a light chain variable region (VL) comprising FR-L1, CDR-L1, FR-L2, CDR-L2, FR-L3, CDR-L3, and FR-L4
    wherein the CDR-L1 region comprises an amino acid sequence according to the formula:

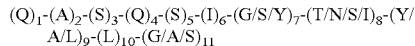

wherein the CDR-L2 region comprises an amino acid sequence according to the formula:

and wherein the CDR-L3 region comprises an amino acid sequence according to the formula:

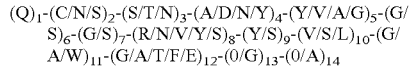

In one preferred embodiment, the antibody of the invention comprises a serine at position 2 of CDR-L3.

Preferably, an antibody according to the invention is a humanized antibody comprising a CDR-H1 region comprising SEQ ID NO 16, a CDR-H2 region comprising SEQ ID NO: 22, a CDR-H3 region comprising SEQ ID NO: 28, and a CDR-L1 region comprising SEQ ID NO: 34. a CDR-L2 region comprising SEQ ID NO: 40, and a CDR-L3 region comprising SEQ ID NO: 46.

The present invention also encompasses an antibody that specifically binds to HER2, or a fragment or derivative thereof or a polypeptide that contains at least a portion of said antibody that is sufficient to confer HER2 binding specificity, wherein said antibody binds to the human Fc receptor and induces FcR mediated signaling pathways.

Preferably, the antibodies according to the invention show an increased induction of FcR mediated signaling pathway, when compared to commercially available antibodies.

Surprisingly, the inventors identified several molecules that show at least 50-fold increase (FoI: Fold of induction) of FcγRIIIa mediated activity (cf. FIG. 2c), Example 1), i.e. at least a 2-fold higher activation of the NFAT pathway than trastuzumab. Trastuzumab exhibits a maximum Fold of induction (FoI) of 26 (cf. FIG. 2a)).

More specifically, the antibody according to the invention may increase the Fc receptor signaling activity in an FcγRIIIa assay by at least 10-fold, preferably at least 20-fold, more preferably at least 50-fold, most preferably 70-fold or more (cf. Example 1, FIG. 2b) c)).

It is preferred that an antibody according to the invention increases the Fc receptor signaling activity in an FcγRIIIa assay by 17-fold, preferably by 22-fold, more preferably by 50-fold and most preferably by 70-fold.

The antibodies according to the invention are also more potent as commercially available antibodies.

In SBKR-3 cells, the antibodies according to the invention, show a stimulation of FcR signaling that is preferably more than 100-fold, more preferably more than 110-fold, 120-fold and more preferably more than 130-fold at an EC50 of 52 ng/ml. A preferred antibody may increase FcR signaling by 132-fold at an EC50 of 52 ng/ml (cf. FIG. 6). This reflects a much higher signaling potency as Trastuzumab. Trastuzumab exhibits a comparable increase of signaling at an EC50 of 81 ng/ml.

This increased activity in comparison to conventional antibodies used in cancer therapy clearly shows its superiority and outstanding potential for the use in the treatment of HER2-mediated diseases.

In order to find novel, more effective monoclonal antibodies than those that are commercially available and conventionally used in cancer therapy, the inventors selected the most promising candidate antibodies and tested them in competition assays (Example 2).

Surprisingly, several molecules were found to bind to different epitopes as the gold-standard antibodies for breast cancer therapy, trastuzumab (TZ) and pertuzumab (PZ), i.e. exhibiting a different and unique mode of action. In combination with their increased activity in NFAT pathway stimulation assays (Example 1, FIG. 2), the differential binding characteristic makes them ideal novel reagents for the use in treating HER2-mediated diseases.

Therefore, the antibody according to the invention binds to a different epitope than trastuzumab. Preferably, the antibody according to the invention also bind to a different epitope than pertuzumab.

This means that the antibody according to the invention does not compete with trastuzumab in an epitope competition assay (FIG. 3).

Also preferred is an antibody according that does not compete with pertuzumab in an eptitope competition assay. With the antibodies designated as B106 and B115 being an exception, it is preferred that the antibodies do not compete with pertuzumab in an epitope competition assay (FIG. 3).

The antibodies according to the invention have the advantage to be very potent when it comes to binding to their target. They exhibit a strong binding capacity to their antigen, HER 2, but not to other receptors. The binding properties of the antibodies were studied in biochemical enzyme-linked immunosorbent assays (ELISA—cf. Example 3 and 4), and are exemplified in FIGS. 4, 5 and 7.

Preferred antibodies according to the invention, show a half maximal effective concentration (EC50) of less than 8 ng/ml, preferably of more than 6 ng/ml in experiments as described in Example 3). A preferred antibody, MABD B100, shows an EC50 of 5.2 ng/ml which is comparable to the EC50 of Trastuzumab and Pertuzumab (cf. FIG. 4).

Strikingly, the antibodies according to the invention also show a very strong binding to their antigen in experiments in which HER 2 is expressed in the SK-BR-3 cell line (cf. Example 5). Preferably, the antibodies exhibit an EC50 of less than 100 ng/ml, preferably less than 80 ng/ml. A preferred antibody according to the invention, MABD B100, shows an EC50 of 78 ng/ml which is comparable to the EC50 of Trastuzumab and Pertuzumab.

The antibodies according to the invention are also very specific in their binding properties. The show a strong binding to HER 2, but not to the homologous receptors HER1, HER3 or HER 4. This is examplied in FIG. 7. Strikingly, the inventors found that this is independent of the concentrations used. All antibodies tested show specific binding to HER2 within the concentration range of 1 ng/mL to 2000 ng/mL. Even at a concentration of more than 100-fold the EC50 of HER2 ELISA, no signal of binding to HER1, HER3 and HER4 was detected.

The inventors also found that the antibodies according to the invention do not only bind to human HER2, but may also be capable of binding to HER2 orthologues. It is preferred that antibodies according to the invention show strong binding to human and cynomolgus HER2 receptors. They may show partial binding to rat HER2 receptor. As it is shown in FIG. 7b), the binding of various antibody according to the invention, to human and cynomolgus HER2 receptors was at a comparable strenght, with similar EC50 values and the antibodies tested also showed a partial reactivity for rat HER2 (EC50>100 ng/mL), but no reactivity to murine HER2.

Surprisingly, and in contrast to commercially available antibodies and antibodies of prior art, the inventors found that the antibodies of this invention are capable of inducing apoptosis with an efficacy comparable to a cytotoxic drug like camptothecin. This is an outstanding activity that will be additive to the activity of other HER2 antibodies with different modes of action. There is no risk for additional toxicities. In contrast to Trastuzumab and Pertuzumab, the antibodies of the invention are capable of inducing apoptosis in at least 60%, preferably more than 65%, more than 70%, 75%, 80% and most preferred more than 85% of cells in SK-BR-3 cell line experiments compared to the positive control camptothecin. In one embodiment of the invention, the antibody shows an induction of apoptosis in 75% of cells, in contrast to only 10% for Trastuzumab and 12% for Pertuzumab (FIG. 8).

As said before, a monoclonal antibody according to the invention can be rabbit antibody. Preferably, it is a rabbit/human chimeric antibody. In a further preferred version, the antibody is a humanized antibody.

The humanized versions of the antibodies according to the invention maintain the favorable properties of their chimeric versions. For example, they remain their strong binding capacity and potency. Preferred humanized antibodies according to the invention show an EC50 of less than 10 ng/ml. In other embodiments, the antibody exhibits an EC50 of less than 9 ng/ml, less than 8 ng/ml, less than 7 ng/ml or less than 6 ng/ml, most preferred of 5.3 ng/ml. FIG. 9 shows examples of some of the preferred antibodies of the invention and their potency.

Also, the humanized versions of the antibodies according to the invention show strong binding capacity in SK-BR-3 experiments (cf. e.g. FIG. 10, Example 4). Preferred humanized antibodies according to the invention show an EC50 of less than 80 ng/ml. In other embodiments, the antibody exhibits an EC50 of less than 70 ng/ml, less than 60 ng/ml, less than 50 ng/ml or less than 40 ng/ml. or most preferred, less than 20 ng/ml. FIG. 10 shows example of some of the preferred antibodies of the invention and their potency.

The humanized antibodies according to the invention are also capable of inducing strong Fcγ-receptor signaling. Preferably, the Fcγ signaling is comparable to the signaling of the chimeric versions of the antibodies or more potent. It is also preferred that the induction of Fcγ signaling is stronger as for commercially available antibodies. In certain embodiments of the invention, the humanized antibodies have an EC50 of less than 300 ng/ml, preferably less than 200 ng/ml, less than 100 nt/ml, less than 95 ng/ml and most preferably less than 60 ng/ml.

As noted before, in contrast to commercially available antibodies and antibodies of prior art, the antibodies of this invention are capable of inducing apoptosis. This holds also true for the humanized version of the antibodies. The humanized antibodies of the invention show an induction of apoptosis of at least 60%, preferably more than 65%, more than 70%, 75%, 80% and most preferred more than 85% (FIG. 12, Example 7).

Strikingly and in contrast to the commercially available antibodies the inventors surprisingly found that the antibodies of the invention are capable of greatly reducing tumor burden in mice. In a HTM-SK-BR-3 tumor model, the antibodies according to the invention are capable of reducing the size of a tumor and the amount of cancer cells dramatically, in contrast to Trastuzumab and Pertuzumab.

Preferred antibodies of the invention can reduce the tumor cell number by more than 80%, preferably more that 85% and most preferred of more than 90%, when compared to Trastuzumab. (cf. FIG. 13).

The inventors found a strong anti-tumor and anti-metastatic activity of the antibodies according to the invention also when analyzing histological sections and tumor cell number of different tissues via flow cytometry. In contrast to commercially available antibodies such as Trastuzumab and Pertuzumab and other antibodies of prior art, the antibodies of the invention strongly reduce tumor cell numbers. For example, tumor cell number is reduced in lung, liver and brain tissue after treatment with said antibodies (cf. FIGS. 14a) and b)).

Furthermore, the antibodies of the invention can efficiently inhibit metastasis of tumor cells, in contrast to commercially available antibodies and to other antibodies of prior art. For example, the antibodies can inhibit the dissemination of tumor cells into the bone marrow in contrast to Trastuzumab and Pertuzumab (FIG. 15).

Due to the specific and favorable properties, the antibodies according to the invention are particularly suited in the treatment of a disease in which the dysregulation of their target antigen is the underlying reason. Due to these specific properties, they are much better suited than commercially available antibodies and other antibodies of prior art.

Therefore, the antibodies according to the invention are especially useful for the treatment of diseases where the dysregulation of the HER2 is the underlying reason.

Therefore, the invention also encompasses an antibody according to the invention for the use in the treatment of a HER-2 mediated disease.

Thus, the present invention also relates to a method of treating an HER-2 mediated disease in a patient, comprising administering to a patient a pharmaceutically effective amount of the antibody according to the invention.

Moreover, the present invention relates to a pharmaceutical composition comprising a pharmaceutically acceptable carrier and a therapeutically effective amount of the antibody according to the invention.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

One aspect of the invention is a pharmaceutical composition according to the invention for use in the treatment of cancer, as defined in this application.

Another aspect of the invention is a method of treating an HER-2 mediated disease in a patient, comprising administering to a patient the pharmaceutical composition according to the invention. Such HER-2 mediated diseases may include cancer.

The term "cancer" as used herein may be, for example, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, colon cancer, lung cancer, or pancreatic cancer. Most preferably the cancer is breast cancer.

EXAMPLES

The following examples are used in conjunction with the figures and tables to illustrate the invention.

Example 1: FcγRIIIa Signaling Assay

The FcγRIIIa signaling assay, which is commercially available e.g. from Promega, allows for early detection of FcγRIIIa receptor signaling, thus for effective antibody candidate selection.

Assay Principle:

Target cells (Jurkat), exhibiting the respective antigen (HER2), are incubated with sample antibodies and JIMT-1 cells. The Jurkat cell line stably expresses the FcγRIIIa receptor, V158, possessing a high affinity to human IgG Fc fragment and contains a NFAT-RE-Promotor site, allowing for the induction of luciferase expression. Upon binding of the antibody to the target (HER2 expressing) cells, Fc mediated binding of the antibody to the FcγRIIIa receptor, activates the NFAT pathway, thus the expression of luciferase. Addition of the luciferase substrate (Luciferin), activates a pathway leading to the photoluminescence, which can be measured, and correlated qualitatively and semi-quantitatively to the binding of the antibody to the receptor, i.e. to its immunological activity. Signal strength of Luciferase correlates with the number of receptors activated.

Assay Procedure

Day 1

Addition of, for example, 7500 or 15000 JIMT-1 cells in 25 μl medium, into each well of a microtiter plate.

Incubation of cells for 20 to 24 hours at 37° C. and 5% $CO_2$.

Day 2

Equilibrating of Luciferase Assay buffer and Luciferase substrate to room temperature.

Manufacture of FcγRIIIa Assay Puffers:

Thawing of FCS with small amounts of IgG ("low IgG FCS" Hyclone der Firma Thermo Scientific SH 30898.03) at 37° C. in a water bath.

Addition of the "low IgG FCS" to DMEM cell culture medium (final concentration: 4%) and Warming up to 37° C. in the water bath.

Concomitant:

Removal of 23 μL medium from each well with a pipette robot (CyBi-Well vario, CyBio).

Addition of 16 μL sample antibody (diluted in "low IgG FCS" medium) and 84 effector cell-suspension (c=500 000/mL, 4000 cells/well).

Incubation for 6 hours, followed by addition of 20 μL Luciferase-assay-reagent (buffer and Substrat, Promega Corp.) and incubation for 10 minutes at room temperature.

Photometric measurement of luminescence (Tecan infinite M1000 PRO)

Substraction of random luminescence, resulting from an unspecific, spontaneous activation of the NFAT pathway:

FoI=(RLU-sample–RLU-blanc):(RLU-effector–RLU-blank)

Sample: antibody sample

Blanc: blind value (buffer only)

Effector: effector cells in medium/buffer without antibody

FoI: signal-to-blanc ratio as x-fold activation (fold of induction)

RLU: photometric luminescence (relative luminescence units)

Candidate antibodies were selected in respect to their Fold induction (FoI) of FcγRIIIa activation for the subsequent generation of chimeric antibodies. The resulting recombinant antibodies were then tested in follow-up experiments.

Example 2: Epitope Competition Assay

Assay Principle

NUNC Maxisorp 384 well microtiter-plates are coated with anti-human Fc, which binds to the monoclonal reference antibody. This plate is designated as "assay plate".

Pre-incubation of the sample antibody with the target antigen (here: HER2, marked with a His-tag) and with an anti-his antibody (marked with POD)

Addition of the pre-incubation mix to the assay plate.

Materials:

Plates: Plate 1: 384 well NUNC Maxisorp plates; Cat. No. 464718 (Assay plate)

Plate 2: Pre-incubate plate: PP-Plate either from Axygen or Deepwell 384 plate

Coating Ab: Goat Anti-Human IgG (Fc specific); Sigma; Cat. No. I 2136; assay concentration: 0.5 μg/ml Proteins: Recombinant Human ErbB2/HER2 Fc Chimera; R&D Systems; Cat. No. 1129-ER; working conc.: volume dependent (assay conc. 0.3 μg/mL)

Standard Abs: Herceptin; Roche; Conc: dilution dependent;

Detection Ab: Monoclonal Anti-polyHistidine Peroxidase Conjugate; Sigma; Cat. No. A7058; working conc.: volume dependent (see 5.1.1/assay conc. 0.5 μg/mL/e.g. for (90+5+5) μL=20*0.5 μg/mL=6 μg/mL)

PBS: Buffers in a Box, Premixed PBS Buffer, 10×; Roche Applied Sciences; Cat. No. 11666789001

BSA: Bovine Serum Albumin Fraction V from bovine serum; Roche Applied Sciences; Cat. No. 10735086001

Tween 20: Tween 20; Sigma-Aldrich; Cat. No. P1379

TMB: TMB Solution; Merck; Cat. No. CL07

HCl: 1M Titripur Hydrochloric Acid; Merck; Cat. No. 1090571000

ELISA Buffer: PBS, 0.5% BSA, 0.05% Tween

Wash Buffer: PBS, 0.05% Tween

Block Buffer: PBS, 2% BSA, 0.05% Tween

Assay Procedure

1. Coating of NUNC Maxisorp plates with 20 μl goat anti human IgG (Fc specific) in PBS and incubation for 1 hour at room temperature (plate 1).
2. 3 washing steps with 90 μl washing buffer per plate
3. Incubation of the plate for 1 hour at room temperature with 90 μl blocking buffer
4. 3 washing steps with 90 μl washing buffer per plate
5. Incubation of the plate with 20 μl primary antibody (0.2 μg/ml) in ELISA buffer for 1 h at RT. Concomitant manufacture of the pre-incubation mix in a different plate (plate 2): Mixing of 90 μl of the sample antibody in ELISA buffer (working concentration: >2 μg/ml; same concentration for the control antibody), respectively only ELISA buffer (blank) with 5 μl of protein with HIS-tag (e.g. HER2-HIS-tag). Addition of 5 ml anti HIS POD-antibody and incubation of the mix for 1 h at room temperature.
6. 3× washing of plate with primary antibody with 90 μl washing buffer.
7. Addition of 20 μl of the pre-incubation mix from plate 2 into the wells of plate 1 and incubation for 1 h at room temperature
8. 6× washing with washing buffer
9. Addition of 25 μl TMB to each of the wells.
10. After sufficient color development, stopping of the reaction by 25 μl HCl.
11. Measurement of the absorption at 450 nm/620 nm.

Example 3: HER 2 Biochemical ELISA (Protocol 1)

Materials:
Plates: 384 well NUNC Maxisorp plates; NUNC; Cat. No. 464718
Coating Proteins:
  human Her1 (Recombinant Human EGFR/ErbB1 Fc Chimera; R&D Systems; Cat. No. 344-ER)
  human Her2 (Recombinant Human ErbB2/HER2 Fc Chimera; R&D Systems; Cat. No. 1129-ER)
  human Her3 (Recombinant Human ErbB3/Her3 Fc Chimera; R&D Systems; Cat. No. 348-RB)
  human Her4 (Recombinant Human ErbB4/HER4 Fc Chimera; R&D Systems; Cat. No. 1131-ER)
  cyno Her2 (Cynomolgus HER2/ErbB2 Protein; Sino Biological; Cat. No. 90295-C08H)
  rat Her2 (Rat HER2/ErbB2 Protein; Sino Biological; Cat. No. 80079-RCCH)
  mouse Her2 (Mouse Her2/ErbB2 Protein; Acro Biosystems; Cat. No. ER2-M5220)
Primary Abs: Trastuzumab
  Pertuzumab
  MABD B100
  MAB-16-0160
  MAB-16-0161
  MAB-16-0163
  MAB-16-0165
Detection Ab: anti-human Fab2 POD-Antibody; AbD Serotec; STAR126P
PBS: Buffers in a Box, Premixed PBS Buffer, 10×; Roche Applied Sciences; Cat. No. 11666789001
BSA: Bovine Serum Albumin Fraction V from bovine serum; Roche Applied Sciences; Cat. No. 10735086001
Tween 20: Tween 20; Sigma-Aldrich; Cat. No. P1379
TMB: TMB Solution; Invitrogen; Cat. No. SB02
HCl: 1M Titripur Hydrochloric Acid; Merck; Cat. No. 1090571000
ELISA Buffer: PBS, 0.5% BSA, 0.05% Tween
Wash Buffer: PBS, 0.1% Tween
Block Buffer: PBS, 2% BSA, 0.05% Tween
Samples: Dilution in ELISA buffer is project dependent (for high concentrated IgGs 1:2 dilution is recommended)

Procedure:
1. Dilute desired coating protein to 0.5 µg/mL in PBS and add 12.5 µl to a 384 well NUNC Maxisorp plate.
2. Incubate for 1 h at room temperature.
3. Wash 3× with Wash Buffer.
4. Add 90 µL Block buffer to each well and incubate for 1 h at room temperature.
5. Wash 3× with Wash Buffer.
6. Add 12.5 µL of the desired primary antibody diluted in ELISA buffer to the desired concentration.
7. Incubate for 1 h at room temperature.
8. Wash 3× with Wash Buffer.
9. Add 12.5 µL of detection antibody diluted 1:5000 in Elisa Buffer, and incubate for 1 h at room temperature.
10. Wash 6× with Wash Buffer.
11. Add 15 µl TMB.
12. Add 15 µL HCl after sufficient development time.
13. Read absorbance at 450 nm/620 nm.
14. Analyze data with Excel Fit (Fit Model: 205, Pre-Fit for all 4 parameters, no Constrains on any parameter, $EC_{50}$=parameter C)

Example 4: Cell Binding to SK-BR-3 (Protocol 2)

Materials:
Cell culture plates: Black, 384 well, clear and flat bottom Corning Cell culture plates; Corning; Cat. No. 3764
Cells: SK-BR-3; ATCC; Cat. No. HTB-30
Primary Ab: Trastuzumab
  Pertuzumab
  MABD B100
  MAB-16-0160
  MAB-16-0161
  MAB-16-0163
  MAB-16-0165
Detection Ab: AF488-conj. AffiniPure α-HuIgG (H&L) Fragm. Speci.; Dianova; Cat. No. 109-546-003
Fluorescent dye: Hoechst; Invitrogen; Cat. No. H3570
FCS: HyClone Fetal Bovine Serum defined; Thermo Scientific; Cat. No. SH 30070.03
Cell medium: Mc Coy's with stab. Glutamine, with 2.2 g/l $NaHCO_3$; PAN Biotech; Cat. No. P04-06500+10% FCS
PBS: Buffers in a Box, Premixed PBS Buffer, 10×; Roche Applied Sciences; Cat. No. 11666789001
Tween 20: Tween 20; Sigma-Aldrich; Cat. No. P1379
Cell wash buffer: PBS, 0.05% Tween Procedure:
1. In a cell culture plate, add 20 µL of primary antibody diluted in cell medium to the desired concentration/-s.
2. In the same wells, seed cells (1.000 cells/well) in 20 µL cell medium.
3. Incubate for 4 h or overnight at 37° C. and 5% CO2.
4. Wash three times with 75 µl cell wash buffer.
5. Dilute detection antibody in cell medium to a concentration of 250 ng/mL and add 20 µl to the tested wells.
6. Incubate for 4 h at 37° C. and 5% CO2.
7. Dilute the fluorescent dye in cell medium to a concentration of 22.5 µg/mL, and add 5 µl to the tested wells.
8. Incubate for 10 min-1 h at room temperature.
9. Analyze binding of antibodies to cells with a CellInsight™ High Content Screening Platform (Min. Objects per Well: 250 cells)
10. Analyze data with Excel Fit (Fit Model: 205, Pre-Fit for all 4 parameters, no Constrains on any parameter, $EC_{50}$: parameter C)

Example 5: Fcy-receptor Signaling (Protocol 3)

Materials:
Plates: White flat-bottom 384-well assay plates with lid; Corning; Cat. No. 3570
Target cells: SKBR-3; ATCC; Cat. No. HTB-30
Effector cells: ADCC Bioassay Effector cells; Promega; Cat. No. G7011
Standard mAb: Trastuzumab
  Pertuzumab
  MABD B100
  MAB-16-0160
  MAB-16-0161
  MAB-16-0163
  MAB-16-0165
ADCC assay buffer: RPMI 1640 Medium & low IgG serum; Promega; Cat. No. G7010
FCS: HyClone Fetal Bovine Serum defined; Thermo Scientific; Cat. No. SH 30070.03
Target cell medium: Mc Coy's with stab. Glutamine, with 2.2 g/l $NaHCO_3$; PAN Biotech; Cat. No. P04-06500+10% FCS Luciferase assay reagent: BioGlo™ Luciferase Assay Buffer & BioGlo™ Luciferase Assay Substrate; Promega; Cat. No. G7010

Procedure:

Day 1:
1. Seed target cells: 2500 cells/well in 25 μL target cell medium
2. Incubate for 20-24 h, 37° C., 5% CO2.

Day 2:
3. Prepare Luciferase assay reagent according to manufacturer's instructions.
4. Prepare ADCC assay buffer according to manufacturer's instructions.
5. Remove 23 μL media from all wells of assay plates. Add gently 8 μL of pre-warmed ADCC assay buffer per well to the plate.
6. Dilute desired primary antibodies in ADCC assay buffer to the desired concentrations, and add 8 μL of the antibody dilutions to wells. As blank add ADCC assay buffer. Store plates on bench.
7. Thaw effector Cells in water bath 37° C. ($13 \times 10^6$ cells/vial; do not invert).
8. Gently mix cells by pipetting. Add 630 μL of cell suspension to 24.57 mL of pre-warmed ADCC assay buffer.
9. Add 8 μL of effector cell suspension per well to the plate (4000 cells/well).
10. Cover plates and incubate for 6 h at 37° C., 5% CO2.
11. Remove plates from incubator and equilibrate to room temperature (15 min).
12. Add 20 μL of Luciferase assay reagent to all wells in test.
13. Incubate at room temperature for 5-30 min.
14. Measure luminescence using a plate reader and calculate results according to BioGlo™ assay manufacturer's instructions.
15. Analyze data with Excel Fit (Fit Model: 205, Pre-Fit for all 4 parameters, no Constrains on any parameter, EC50: parameter C)

Example 6: Apoptosis Assay (Protocol 5)

Materials:
Cell culture plates: 6-well cell culture plates, Nunclon surface; Nunc; Cat. No.: 140685
Assay plates: 96-DWP DNA LoBind plates; Eppendorf; Cat. No.: 0030602.307
Cells: SKBR-3; ATCC; Cat. No. HTB-30
FCS Fetal Bovine Serum South Africa Low IgG (PAN; Cat. No. 1552-P120909)
Cell- and Assay-Medium: DMEM; PAN; Cat. No.: PO4-04510+5% FCS
Primary Ab: Pertuzumab
 Trastuzumab
 MABD B100
 MAB-16-0160
 MAB-16-0161
 MAB-16-0163
 MAB-16-0165
Reagents: (A) Annexin V FITC-conjugated; Immunotools; Cat. No.: 31490013X2
(C) Camptothecin; Sigma-Aldrich; Cat. No.: C9911
(D) DRAQ7™; Abcam; Cat. No.: ab109202
Binding buffer: 0.1M HEPES; Gibco; Cat. No.: 15630-106+ 1.4M NaCl; Sigma; Cat. No.: S7653-1 kg+25 mM CaCl2; Fluka; Cat. No.: 21114-1L Protocol:
1. Seed cells ($8 \times 10^4$ cells/well) in 2 mL cell medium per well of cell culture plates. Incubate 72 h; 37° C.; 5% CO2.
2. Remove medium.
3. Add to plate, 2 mL assay-medium (control wells) or primary antibody diluted to desired concentration in assay-medium.
4. Incubate 48 h; 37° C.; 5% CO2.
5. Add 5 μl Camptothecin (2 mM) to one or more wells as positive control.
6. Incubate 24 h; 37° C.; 5% CO2.
7. Transfer supernatant from each well to a separate 15 ml-tube
8. Wash each well with 1.5 ml PBS and transfer supernatant to its same respective 15 ml-tube.
9. Add 0.5 ml Trypsin to each well, incubate at 37° C., then stop with 1.5 ml cell-medium and transfer all liquid to its respective 15 ml-tube.
10. Add 5 ml PBS to each 15 ml-tube.
11. Centrifuge 15 ml-tubes at 300 g, 3 min, 4° C., and discard supernatant
12. Add 140 μL precooled Binding Buffer (4° C.), re-suspend and transfer 70 μl to assay plates.
13. Add 5 μL precooled Annexin (4° C.), mix and incubate 20 min on ice/dark.
14. Add 2 μL DRAQ7™ diluted 1:100 in binding buffer.
15. Add 120 μL precooled binding buffer (4° C.), mix and incubate 7 min on ice/dark.

Perform flow cytometry analysis.

FIGURE LEGEND

FIG. 1: Sequences (Amino Acids in One Letter Code)
Complete sequences of Variable Regions (VR):

| Heavy chain: | VH complete: | SEQ ID NO: 1-6 and SEQ ID NO: 100-101 |
|---|---|---|
| Light chain: | VL complete: | SEQ ID NO: 7-12 and SEQ ID NO: 102-104 |

The VL sequences may comprise a Cysteine to Serine mutation at position 90.

Complementary Determining Regions (CDR):

| Heavy Chain: | CDR-H1: | SEQ ID NO: 13-18 |
|---|---|---|
| | CDR-H2: | SEQ ID NO: 19-24 |
| | CDR-H3: | SEQ ID NO: 25-30 |
| Light Chain: | CDR-L1: | SEQ ID NO: 31-36 |
| | CDR-L2: | SEQ ID NO: 37-42 |
| | CDR-L3: | SEQ ID NO: 43-48 |

Framework Regions (FR):

| Heavy Chain: | FR-H1: | SEQ ID NO: 49-54 |
|---|---|---|
| | FR-H2: | SEQ ID NO: 55-60 |
| | FR-H3: | SEQ ID NO: 61-66 |
| | FR-H4: | SEQ ID NO: 67-72 |
| Light Chain: | FR-L1: | SEQ ID NO: 73-78 |
| | FR-L2: | SEQ ID NO: 79-84 |
| | FR-L3: | SEQ ID NO: 85-90 |
| | FR-L4: | SEQ ID NO: 91-96 |

Constant Regions (CR):

| Light Chain: | CR-L: | SEQ ID NO: 97 |
|---|---|---|
| Heavy Chain: | CR-H: | SEQ ID NO: 98-99 |

FIG. 2: Antibody Selection Through FcγRIIIa Signaling Assay

Details of the assay procedure are disclosed in example 1. Candidate antibodies were selected in respect to their Fold of Induction (FoI) of FcγRIIIa signaling.
a) FoI of FcγRIIIa signaling by trastuzumab, in dependence of the antibody concentration. The maximum FoI is approximately 26.
b) FoI of FcγRIIIa signaling by a selected candidate antibody. The maximum FoI is >75.
c) Candidate antibodies were selected according to their FoI to produce recombinant chimeric antibodies. Shown are FcγRIIIa signaling results of the chimeric antibodies in follow-up experiments.

FIG. 3: Epitope Competition Assay

None of the selected antibodies according to the invention compete with trastuzumab for its epitope, while Herceptin (positive control) reduces the POD signal by over 80% (+++). As positive control, the presence of pertuzumab in the pre-incubation mix reduces the POD signal over 80% (+++) in a concentration dependent manner. B106 shows epitope competition with pertuzumab, while B115 shows partial competition for the pertuzumab epitope. No epitope competition is observed with any other of the selected candidate antibodies according to the invention.

FIG. 4: HER2 Biochemical ELISA

The results shown were obtained in experiments as described in Example 3.

A preferred antibody according to the invention, MABD B100, shows an EC50 of 5.2 ng/ml which is comparable to the EC50 of Trastuzumab and Pertuzumab.

FIG. 5: Binding to SK-BR-3 Cell Line

The results shown are from experiments as described in Example 4.

A preferred antibody according to the invention, MABD B100, shows an EC50 of 78 ng/ml which is comparable to the EC50 of Trastuzumab and Pertuzumab.

FIG. 6: Fcγ-receptor Signaling

The results shown were obtained in experiments as described in Example 5.

A preferred antibody according to the invention, MABD B100, shows a stimulation of FcR signaling of 132-fold at an EC50 of 52 ng/ml. Trastuzumab exhibits a comparable signaling strength at an EC 50 of 81 ng/ml. This highlights the improvement in potency over commercially available antibodies.

FIG. 7: Receptors Binding in ELISA Experiments

Antibody binding to different receptors was tested in biochemical ELISA experiments. The experiments were carried out according to the protocol as detailed in Example 3 (Protocol 1).
  a) Binding to Homologues HER Receptors
All tested antibodies show specific binding to HER2 within the concentration range of 1 ng/mL to 2000 ng/mL. Even at a concentration of more than 100-fold the $EC_{50}$ of HER2 ELISA, no signal of binding to HER1, HER3 and HER4 was detected.
  b) Binding to Orthologues of HER2
The binding of antibody according to the invention, to human and cynomolgus HER2 receptors was comparable, with similar $EC_{50}$ values. The antibodies showed a partial reactivity for rat HER2 ($EC_{50}$>100 ng/mL), but no reactivity to murine HER2.

FIG. 8: Apoptosis Induction on SK-BR-3 Cell Line

FIG. 8 shows the results of experiments that were carried out according to the protocol of Example 7. Apoptosis induction was measured as Annexin staining after in-vitro incubation. Camptothecin was used as positive control (set as 100%). MABD B100 shows a uniquely strong apoptosis induction (75%), in contrast to Trastuzumab (10%) and Pertuzumab (12%).

FIG. 9: HER2 Biochemical ELISA of Humanized Variants

Shown are the results of experiments that were carried out according to Example 3.

Four preferred humanized monoclonal antibody candidates maintain the favorable in vitro properties of the chimeric version.

FIG. 10: Binding to SK-BR-3 Cell Line of Humanized Mab Variants

Experiments were carried out according to the protocol as described in Example 4.

The four humanized leads maintain in vitro properties of the chimeric version.

FIG. 11: Fcγ-receptor Signaling of Humanized Mab Variants

Experiments were carried out according to the protocol as described in Example 5. The four humanized leads maintain in vitro properties of the chimeric version.

FIG. 12: Apoptosis Induction of Humanized Mab Variants

Experiments were carried out according to the Protocol as described in Example 7. Camptothecin (second row) was used as positive control (set as 100%). The preferred humanized antibodies according to the invention show a strikingly strong apoptosis induction (68% to 83%).

FIG. 13-15: In Vivo Experiments

In vivo experiments were carried out in well-established human transplant mouse models (HTM) (Wege et al. 2011/2014/2016). Specifically, the HTM model with the SK-BR-3 tumor cell line was employed. This model is resistant to trastuzumab treatment and shows strong dissemination and metastasis. The experiments comprised 9 weeks of establishment of immune system, tumor and metastases and 12 weeks of treatment with 5 mg/kg/week i.p. antibody or placebo.

FIG. 13: In Vivo Profile of MABD B100: Tumor Burden after Treatment

Animals with a functional human immune system were analyzed at the end of treatment.

Treatment with a preferred antibody according to the invention, MABD B100, resulted in a strong reduction of tumor burden compared to treatment with the control, trastuzumab and pertuzumab antibodies.

Remission (4/5) or >95% reduction (1/5) by MABD B100 treatment: p=0.037 vs. control No effect with trastuzumab and pertuzumab treatment: not significant FIG. 14: In Vivo Profile of MABD B100: Anti-Tumor and Anti-Metastatic Activity Experiments were carried out in the HTM-SK-BR-3 model and results were evaluated qualitatively (Y/N): Metastases by IHC (a) and by flow cytometry (b)
  a) HER2+ Tumor cells in histological sections
  b) HER2+ tumor cells analyzed by flow cytometry
Column 2: Control: Animals with a functional human immune system at the end of treatment
Column 3: Treatment with Trastuzumab Column 4: Treatment with the MABD B100
Column 5: Treatment with Pertuzumab
Colum 6+7: Historical data included from Wege et al. 2016

FIG. 15: In Vivo Profile of MABD B100: Dissemination of Tumor Cells to Bone Marrow Experiments were carried out in the HTM-SK-BR-3 model and results were evaluated qualitatively (Y/N). Cells were isolated from bone marrow and cultivated. After expansion, cells were tested for resistance to treatment by FACS.

Control: Animals with a functional human immune system at the end of treatment.

MABD B100 shows an efficient inhibition of dissemination of tumor cells to the bone marrow.

---

The invention claimed is:

1. Monoclonal antibody that specifically binds to HER2, or a fragment or derivative thereof or a polypeptide that contains at least a portion of said antibody that is sufficient to confer HER2 binding specificity, comprising a VH region and a VL region comprising the respective CDR1, CDR2 and CDR3 regions of an antibody selected from the group consisting of:
   i. B 100 comprising light chain variable region CDR amino acid sequences CDR-L1 of SEQ ID NO: 34, CDR-L2 of SEQ ID NO: 40, and CDR-L3 of SEQ ID NO: 46, and heavy chain variable region CDR amino acid sequences CDR-H1 of SEQ ID NO: 16, CDR-H2 of SEQ ID NO: 22, and CDR-H3 of SEQ ID NO: 28;
   ii. C074 comprising light chain variable region CDR amino acid sequences CDR-L1 of SEQ ID NO: 31, CDR-L2 of SEQ ID NO: 37, and CDR-L3 of SEQ ID NO: 43, and heavy chain variable region CDR amino acid sequences CDR-H1 of SEQ ID NO: 13, CDR-H2 of SEQ ID NO: 19, and CDR-H3 of SEQ ID NO: 25;
   iii. C031 comprising light chain variable region CDR amino acid sequences CDR-L1 of SEQ ID NO: 32, CDR-L2 of SEQ ID NO: 38, and CDR-L3 of SEQ ID NO: 44, and heavy chain variable region CDR amino acid sequences CDR-H1 of SEQ ID NO: 14, CDR-H2 of SEQ ID NO: 20, and CDR-H3 of SEQ ID NO: 26;
   iv. B 106 comprising light chain variable region CDR amino acid sequences CDR-L1 of SEQ ID NO: 33, CDR-L2 of SEQ ID NO: 39, and CDR-L3 of SEQ ID NO: 45, and heavy chain variable region CDR amino acid sequences CDR-H1 of SEQ ID NO: 15, CDR-H2 of SEQ ID NO: 21, and CDR-H3 of SEQ ID NO: 27;
   v. AK57 comprising light chain variable region CDR amino acid sequences CDR-L1 of SEQ ID NO: 35, CDR-L2 of SEQ ID NO: 41, and CDR-L3 of SEQ ID NO: 47, and heavy chain variable region CDR amino acid sequences CDR-H1 of SEQ ID NO: 17, CDR-H2 of SEQ ID NO: 23, and CDR-H3 of SEQ ID NO: 29;
   vi. B 115 comprising light chain variable region CDR amino acid sequences CDR-L1 of SEQ ID NO: 36, CDR-L2 of SEQ ID NO: 42, and CDR-L3 of SEQ ID NO: 48, and heavy chain variable region CDR amino acid sequences CDR-H1 of SEQ ID NO: 18, CDR-H2 of SEQ ID NO: 24, and CDR-H3 of SEQ ID NO: 30.

2. Antibody according to claim 1, further comprising:
   a) a heavy chain variable (VH) region at least 90% identical to a VH region selected from the group consisting of VH regions of SEQ ID NO: 1 to 6 and SEQ ID NO: 100 to 101, and
   b) a light chain variable (VL) region at least 90% identical to a VL region selected from the group consisting of VL regions of SEQ ID NO: 7 to 12 and SEQ ID NO 102 to 104.

3. Antibody according to claim 2, wherein the antibody comprises a heavy chain variable (VH) region that is at least 90% identical to the VH region of SEQ ID NO: 4.

4. Antibody according to claim 2, wherein the antibody comprises a light chain variable (VL) region that is at least 90% identical to the VL region of SEQ ID NO: 10.

5. Antibody according to claim 2, wherein the antibody comprises a VH region selected from the group of VH regions comprising a CDR-H1 region of SEQ ID NO: 13+n, a CDR-H2 region of SEQ ID NO: 19+n and a CDR-H3 region of SEQ ID NO: 25+n, wherein n is a number selected from the group consisting of 0 to 5.

6. Antibody according to claim 2, wherein said antibody comprises a VL region selected from the group of VL regions comprising a CDR-L1 region of SEQ ID NO: 31+n, a CDR-L2 region of SEQ ID NO: 37+n and a CDR-L3 region of SEQ ID NO: 43+n, wherein n is a number selected from the group consisting of 0 to 5.

7. Antibody according to claim 2, wherein said antibody comprises a VH region selected from the group of VH regions comprising a CDR-H1 region of SEQ ID NO: 13+n, a CDR-H2 region of SEQ ID NO: 19+n and a CDR-H3 region of SEQ ID NO: 25+n, and wherein the antibody comprises a VL region selected from the group of VL regions comprising a CDR-L1 region of SEQ ID NO: 31+n, a CDR-L2 region of SEQ ID NO: 37+n and a CDR-L3 region of SEQ ID NO: 43+n, wherein n is a number selected from the group consisting of 0 to 5.

8. Monoclonal antibody according to claim 7, wherein said antibody also binds to the human Fc receptor and induces FcR mediated signaling pathways.

9. Monoclonal antibody according to claim 8, wherein said antibody also binds to the human Fc receptor and induces FcR mediated signaling pathways and binds to the same epitope as an antibody selected from the group of antibodies C074, C031, B106, B100, AK57, B115.

10. The antibody according to claim 8, wherein said antibody increases the Fc receptor signaling activity in an FcγRIIIa assay by at least 10-fold.

11. The antibody according to claim 8, wherein said antibody binds to a different epitope than trastuzumab.

12. The antibody according to claim 8, wherein said antibody does not compete with trastuzumab in an epitope competition assay.

13. The antibody according to claim 8, wherein said antibody does not compete with pertuzumab in an epitope competition assay, except for the antibodies designated as B106 and B115.

14. The antibody according to claim 8, wherein said antibody is capable of inducing apoptosis.

15. The antibody according to claim 8, wherein said antibody is a humanized antibody.

16. The antibody according to claim 8, wherein said antibody is capable of reducing the tumor burden, tumor dissemination and metastasis.

17. A method of treatment of a HER-2 mediated disease comprising administering to a subject in need thereof an effective amount of the antibody according to claim 1 to treat a HER-2 mediated disease.

18. A pharmaceutical composition comprising a pharmaceutically acceptable carrier and a therapeutically effective amount of the antibody according to claim 1.

19. A method of treatment of a HER-2 mediated disease comprising administering to a subject in need thereof an effective amount of the pharmaceutical composition according to claim 18 to treat a HER-2 mediated disease.

20. The antibody according to claim 8, wherein said antibody increases the Fc receptor signaling activity in an FcγRIIIa assay by at least 20-fold.

21. The antibody according to claim 8, wherein said antibody increases the Fc receptor signaling activity in an FcγRIIIa assay by at least 50-fold.

* * * * *

SEQUENCE LISTING

<160> NUMBER OF SEQ ID NOS: 104

<210> SEQ ID NO 1
<211> LENGTH: 116
<212> TYPE: PRT
<213> ORGANISM: Artificial Sequence
<220> FEATURE:
<223> OTHER INFORMATION: recombinant chimeric antibody

<400> SEQUENCE: 1

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asn
            20                  25                  30

Met Gly Trp Val Arg Gln Ala Pro Gly Lys Gly Leu Glu Trp Ile Gly
        35                  40                  45

Ile Ile Ser His Ser Asp Asn Thr Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Gly Ala
                85                  90                  95

Ala Gly Gly Ser Gly Ala Tyr Asn Leu Trp Gly Gln Gly Met Leu Val
                100                 105                 110

Thr Val Ser Ser
        115
```

<210> SEQ ID NO 2
<211> LENGTH: 116
<212> TYPE: PRT
<213> ORGANISM: Artificial Sequence
<220> FEATURE:
<223> OTHER INFORMATION: recombinant chimeric antibody

<400> SEQUENCE: 2

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Asn
            20                  25                  30

Met Ala Trp Val Arg Gln Ala Pro Gly Glu Gly Leu Glu Tyr Ile Gly
        35                  40                  45

Ile Ile Asn Ala Gly Gly Thr Ala Tyr Tyr Ala Ser Trp Ala Lys Gly
    50                  55                  60

Arg Ile Thr Ile Ser Lys Thr Ser Thr Thr Val Asp Leu Lys Ile Ser
65                  70                  75                  80

Ser Pro Thr Ala Glu Asp Thr Ala Thr Tyr Phe Cys Ala Arg Ser Tyr
                85                  90                  95

Thr Ser Asn Ser Gly Ala Phe Asn Ile Trp Gly Pro Gly Thr Leu Val
                100                 105                 110

Thr Val Ser Ser
```

115

<210> SEQ ID NO 3
<211> LENGTH: 114
<212> TYPE: PRT
<213> ORGANISM: Artificial Sequence
<220> FEATURE:
<223> OTHER INFORMATION: recombinant chimeric antibody

<400> SEQUENCE: 3

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Ser Tyr Ala
            20                  25                  30
Met Ser Trp Val Arg Gln Ala Pro Gly Lys Gly Leu Glu Trp Ile Gly
        35                  40                  45
Ile Ile Tyr Ser Gly Gly Asn Ala His Tyr Ala Ser Trp Ala Lys Gly
    50                  55                  60
Arg Phe Thr Ile Ser Arg Thr Ser Thr Thr Val Asp Leu Lys Met Thr
65                  70                  75                  80
Ser Leu Thr Thr Glu Asp Thr Ala Thr Tyr Phe Cys Ala Arg Gly Asp
                85                  90                  95
Asp Ser Ser Gly Leu Arg Leu Trp Gly Gln Gly Thr Leu Val Thr Val
            100                 105                 110
Ser Ser
```

<210> SEQ ID NO 4
<211> LENGTH: 116
<212> TYPE: PRT
<213> ORGANISM: Artificial Sequence
<220> FEATURE:
<223> OTHER INFORMATION: recombinant chimeric antibody

<400> SEQUENCE: 4

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Asn Tyr Gly
            20                  25                  30
Val Ser Trp Val Arg Gln Ala Pro Gly Lys Gly Leu Glu Tyr Ile Gly
        35                  40                  45
Ile Ile Ser Gly Ser Gly Phe Thr Tyr Tyr Ala Ser Trp Ala Lys Gly
    50                  55                  60
Arg Phe Thr Ile Ser Lys Thr Ser Thr Thr Val Asp Leu Lys Ile Thr
65                  70                  75                  80
Ser Pro Thr Thr Lys Asp Thr Ala Thr Tyr Phe Cys Ala Arg Gly Val
                85                  90                  95
Val Pro Gly Tyr Asn Ala Gly Gly Leu Trp Gly Gln Gly Thr Leu Val
            100                 105                 110
Thr Val Ser Ser
        115
```

<210> SEQ ID NO 5
<211> LENGTH: 120
<212> TYPE: PRT
<213> ORGANISM: Artificial Sequence
<220> FEATURE:
<223> OTHER INFORMATION: recombinant chimeric antibody

<400> SEQUENCE: 5

Gln Ser Val Glu Ser Gly Gly Arg Leu Val Thr Pro Gly Thr Pro
1               5                   10                  15

Leu Thr Leu Thr Cys Thr Val Ser Gly Phe Ser Leu Ser Tyr Ala
                20                  25                  30

Met Ser Trp Val Arg Gln Ala Pro Gly Lys Gly Leu Glu Trp Ile Gly
            35                  40                  45

Ile Ile Tyr Ala Ile Ser Asp Asn Thr Trp Phe Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Ala
                85                  90                  95

Leu Tyr Ala Gly Tyr Thr Ala Gly Tyr Tyr Phe Ser Leu Trp Gly Pro
            100                 105                 110

Gly Thr Leu Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: recombinant chimeric antibody

<400> SEQUENCE: 6

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
                20                  25                  30

Tyr Met Cys Trp Leu Arg Gln Ala Pro Gly Lys Gly Leu Glu Trp Val
            35                  40                  45

Ala Cys Ile Tyr Gly Gly Ser Ser Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Gln Ile Tyr Asp Asp Ser Gly Phe Asn Leu Trp Gly Pro
            100                 105                 110

Gly Thr Leu Val Thr Val Ser Ser
        115                 120

<210> SEQ ID NO 7
<211> LENGTH: 110
<212> TYPE: PRT
<213> ORGANISM: Artificial Sequence
<220> FEATURE:
<223> OTHER INFORMATION: recombinant chimeric antibody

<400> SEQUENCE: 7

Asp Ile Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Thr Ala
                20                  25                  30

Leu Gly Trp Tyr Gln Gln Lys Pro Gly Gln Arg Pro Lys Leu Leu Ile
            35                  40                  45

Tyr Gly Ala Ser Asn Leu Glu Phe Gly Val Pro Ser Arg Phe Lys Gly
    50                  55                  60

```
Ser Gly Ser Gly Thr Glu Tyr Thr Leu Thr Ile Ser Asp Leu Glu Ser
 65                  70                  75                  80

Gly Asp Ala Ala Thr Tyr Tyr Cys Gln Cys Ser Ala Tyr Gly Ser Arg
                 85                  90                  95

Tyr Val Gly Gly Phe Gly Gly Thr Glu Val Val Val Lys
            100                 105                 110

<210> SEQ ID NO 8
<211> LENGTH: 110
<212> TYPE: PRT
<213> ORGANISM: Artificial Sequence
<220> FEATURE:
<223> OTHER INFORMATION: recombinant chimeric antibody

<400> SEQUENCE: 8

Asp Val Val Met Thr Gln Thr Pro Ala Ser Val Ser Glu Pro Val Gly
  1               5                  10                  15

Gly Thr Val Thr Ile Lys Cys Gln Ala Ser Gln Ser Ile Gly Asn Ala
                 20                  25                  30

Leu Ala Trp Tyr Gln Gln Lys Pro Gly Gln Pro Pro Lys Leu Leu Ile
             35                  40                  45

Tyr Gly Ala Ser Asn Leu Glu Ser Gly Val Ser Ser Arg Phe Arg Gly
 50                  55                  60

Ser Arg Ser Gly Thr Glu Phe Thr Leu Thr Ile Ser Asp Leu Glu Ser
 65                  70                  75                  80

Ala Asp Ala Ala Thr Tyr Tyr Cys Gln Cys Ser Ala Tyr Gly Ser Val
                 85                  90                  95

Tyr Val Gly Thr Phe Gly Gly Gly Thr Glu Val Val Val Lys
            100                 105                 110

<210> SEQ ID NO 9
<211> LENGTH: 110
<212> TYPE: PRT
<213> ORGANISM: Artificial Sequence
<220> FEATURE:
<223> OTHER INFORMATION: recombinant chimeric antibody

<400> SEQUENCE: 9

Asp Val Val Met Thr Gln Thr Pro Ala Ser Val Ser Glu Pro Val Gly
  1               5                  10                  15

Gly Thr Val Thr Ile Lys Cys Gln Ala Ser Gln Ser Ile Ser Asn Leu
                 20                  25                  30

Leu Ala Trp Tyr Gln Gln Lys Pro Gly Gln Arg Pro Lys Leu Leu Met
             35                  40                  45

Ser Tyr Ala Ser Ser Leu Ala Ser Gly Val Ser Ser Arg Phe Lys Gly
 50                  55                  60

Ser Arg Ser Gly Thr Glu Tyr Thr Leu Thr Ile Ser Asp Leu Glu Cys
 65                  70                  75                  80

Ala Asp Ala Ala Thr Tyr Tyr Cys Gln Cys Thr Asp Val Gly Ser Asn
                 85                  90                  95

Tyr Leu Gly Ala Phe Gly Gly Gly Thr Glu Val Val Val Lys
            100                 105                 110

<210> SEQ ID NO 10
<211> LENGTH: 110
<212> TYPE: PRT
<213> ORGANISM: Artificial Sequence
<220> FEATURE:
<223> OTHER INFORMATION: recombinant chimeric antibody
```

<400> SEQUENCE: 10

```
Asp Ile Val Met Thr Gln Thr Pro Ala Ser Val Ser Glu Pro Val Gly
1               5                   10                  15

Gly Thr Val Thr Ile Lys Cys Gln Ala Ser Gln Gly Ile Ser Thr Ala
            20                  25                  30

Leu Ala Trp Tyr Gln Gln Lys Pro Gly Gln Arg Pro Lys Leu Leu Ile
        35                  40                  45

Tyr Ser Ala Ser Thr Leu Ala Ser Gly Val Ser Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Cys Thr Ala Ala Gly Ser Val
                85                  90                  95

Ser Val Gly Ala Phe Gly Gly Gly Thr Glu Val Val Val Asn
            100                 105                 110
```

<210> SEQ ID NO 11
<211> LENGTH: 112
<212> TYPE: PRT
<213> ORGANISM: Artificial Sequence
<220> FEATURE:
<223> OTHER INFORMATION: recombinant chimeric antibody

<400> SEQUENCE: 11

```
Asp Pro Val Leu Thr Gln Thr Pro Ser Ser Ala Ser Glu Pro Val Gly
1               5                   10                  15

Gly Thr Val Thr Ile Lys Cys Gln Ala Ser Gln Ser Ile Tyr Ser Tyr
            20                  25                  30

Leu Ser Trp Tyr Gln Gln Lys Pro Gly Gln Pro Pro Glu Leu Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ser Ala Thr Tyr Tyr Cys Gln Asn Asn Asn Gly Gly Ser Tyr
                85                  90                  95

Ser Ser Ala Phe Gly Ala Phe Gly Gly Gly Thr Glu Val Val Val Lys
            100                 105                 110
```

<210> SEQ ID NO 12
<211> LENGTH: 112
<212> TYPE: PRT
<213> ORGANISM: Artificial Sequence
<220> FEATURE:
<223> OTHER INFORMATION: recombinant chimeric antibody

<400> SEQUENCE: 12

```
Asp Ile Val Met Thr Gln Thr Pro Ser Ser Val Ser Glu Pro Val Gly
1               5                   10                  15

Gly Thr Val Thr Ile Lys Cys Gln Ala Ser Gln Ser Ile Ser Ile Tyr
            20                  25                  30

Leu Ser Trp Tyr Gln Gln Lys Pro Gly Gln Pro Pro Lys Arg Leu Ile
        35                  40                  45

Tyr Lys Ala Ser Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80
```

```
Ala Asp Ala Ala Thr Tyr Tyr Cys Gln Ser Asn Tyr Gly Ser Gly Ser
                85                  90                  95

Ser Ser Trp Glu Gly Ala Phe Gly Gly Gly Thr Glu Val Val Val Lys
            100                 105                 110

<210> SEQ ID NO 13
<211> LENGTH: 5
<212> TYPE: PRT
<213> ORGANISM: Artificial Sequence
<220> FEATURE:
<223> OTHER INFORMATION: recombinant chimeric antibody

<400> SEQUENCE: 13

Ser Tyr Asn Met Gly
1               5

<210> SEQ ID NO 14
<211> LENGTH: 5
<212> TYPE: PRT
<213> ORGANISM: Artificial Sequence
<220> FEATURE:
<223> OTHER INFORMATION: recombinant chimeric antibody

<400> SEQUENCE: 14

Asn Tyr Asn Met Ala
1               5

<210> SEQ ID NO 15
<211> LENGTH: 5
<212> TYPE: PRT
<213> ORGANISM: Artificial Sequence
<220> FEATURE:
<223> OTHER INFORMATION: recombinant chimeric antibody

<400> SEQUENCE: 15

Ser Tyr Ala Met Ser
1               5

<210> SEQ ID NO 16
<211> LENGTH: 5
<212> TYPE: PRT
<213> ORGANISM: Artificial Sequence
<220> FEATURE:
<223> OTHER INFORMATION: recombinant chimeric antibody

<400> SEQUENCE: 16

Asn Tyr Gly Val Ser
1               5

<210> SEQ ID NO 17
<211> LENGTH: 5
<212> TYPE: PRT
<213> ORGANISM: Artificial Sequence
<220> FEATURE:
<223> OTHER INFORMATION: recombinant chimeric antibody

<400> SEQUENCE: 17

Ser Tyr Ala Met Ser
1               5

<210> SEQ ID NO 18
<211> LENGTH: 6
<212> TYPE: PRT
<213> ORGANISM: Artificial Sequence
<220> FEATURE:
<223> OTHER INFORMATION: recombinant chimeric antibody
```

```
<400> SEQUENCE: 18

Ser Ser Tyr Tyr Met Cys
1               5

<210> SEQ ID NO 19
<211> LENGTH: 16
<212> TYPE: PRT
<213> ORGANISM: Artificial Sequence
<220> FEATURE:
<223> OTHER INFORMATION: recombinant chimeric antibody

<400> SEQUENCE: 19

Ile Ile Ser His Ser Asp Asn Thr Tyr Tyr Ala Ser Trp Ala Lys Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: recombinant chimeric antibody

<400> SEQUENCE: 20

Ile Ile Asn Ala Gly Gly Thr Ala Tyr Tyr Ala Ser Trp Ala Lys Gly
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: recombinant chimeric antibody

<400> SEQUENCE: 21

Ile Ile Tyr Ser Gly Gly Asn Ala His Tyr Ala Ser Trp Ala Lys Gly
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: recombinant chimeric antibody

<400> SEQUENCE: 22

Ile Ile Ser Gly Ser Gly Phe Thr Tyr Tyr Ala Ser Trp Ala Lys Gly
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: recombinant chimeric antibody

<400> SEQUENCE: 23

Ile Ile Tyr Ala Ile Ser Asp Asn Thr Trp Phe Ala Ser Trp Ala Lys
1               5                   10                  15

Gly

<210> SEQ ID NO 24
<211> LENGTH: 18
<212> TYPE: PRT
<213> ORGANISM: Artificial Sequence
<220> FEATURE:
```

<223> OTHER INFORMATION: recombinant chimeric antibody

<400> SEQUENCE: 24

Cys Ile Tyr Gly Gly Ser Ser Ser Thr Tyr Ala Ser Trp Ala
1               5                   10                  15
Lys Gly

<210> SEQ ID NO 25
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 25

Gly Ala Ala Gly Gly Ser Gly Ala Tyr Asn Leu
1               5                   10

<210> SEQ ID NO 26
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 26

Ser Tyr Thr Ser Asn Ser Gly Ala Phe Asn Ile
1               5                   10

<210> SEQ ID NO 27
<211> LENGTH: 9
<212> TYPE: PRT
<213> ORGANISM: Artificial Sequence
<220> FEATURE:
<223> OTHER INFORMATION: recombinant chimeric antibody

<400> SEQUENCE: 27

Gly Asp Asp Ser Ser Gly Leu Arg Leu
1               5

<210> SEQ ID NO 28
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 28

Gly Val Val Pro Gly Tyr Asn Ala Gly Gly Leu
1               5                   10

<210> SEQ ID NO 29
<211> LENGTH: 14
<212> TYPE: PRT
<213> ORGANISM: Artificial Sequence
<220> FEATURE:
<223> OTHER INFORMATION: recombinant chimeric antibody

<400> SEQUENCE: 29

Ala Leu Tyr Ala Gly Tyr Thr Ala Gly Tyr Tyr Phe Ser Leu
1               5                   10

<210> SEQ ID NO 30
<211> LENGTH: 11
<212> TYPE: PRT
<213> ORGANISM: Artificial Sequence

```
<220> FEATURE:
<223> OTHER INFORMATION: recombinant chimeric antibody

<400> SEQUENCE: 30

Asp Gln Ile Tyr Asp Asp Ser Gly Phe Asn Leu
1               5                   10

<210> SEQ ID NO 31
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 31

Gln Ala Ser Gln Ser Ile Ser Thr Ala Leu Gly
1               5                   10

<210> SEQ ID NO 32
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 32

Gln Ala Ser Gln Ser Ile Gly Asn Ala Leu Ala
1               5                   10

<210> SEQ ID NO 33
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 33

Gln Ala Ser Gln Ser Ile Ser Asn Leu Leu Ala
1               5                   10

<210> SEQ ID NO 34
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 34

Gln Ala Ser Gln Gly Ile Ser Thr Ala Leu Ala
1               5                   10

<210> SEQ ID NO 35
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 35

Gln Ala Ser Gln Ser Ile Tyr Ser Tyr Leu Ser
1               5                   10

<210> SEQ ID NO 36
<211> LENGTH: 11
<212> TYPE: PRT
<213> ORGANISM: Artificial Sequence
<220> FEATURE:
```

```
<223> OTHER INFORMATION: recombinant chimeric antibody

<400> SEQUENCE: 36

Gln Ala Ser Gln Ser Ile Ser Ile Tyr Leu Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: recombinant chimeric antibody

<400> SEQUENCE: 37

Gly Ala Ser Asn Leu Glu Phe
1               5

<210> SEQ ID NO 38
<211> LENGTH: 7
<212> TYPE: PRT
<213> ORGANISM: Artificial Sequence
<220> FEATURE:
<223> OTHER INFORMATION: recombinant chimeric antibody

<400> SEQUENCE: 38

Gly Ala Ser Asn Leu Glu Ser
1               5

<210> SEQ ID NO 39
<211> LENGTH: 7
<212> TYPE: PRT
<213> ORGANISM: Artificial Sequence
<220> FEATURE:
<223> OTHER INFORMATION: recombinant chimeric antibody

<400> SEQUENCE: 39

Tyr Ala Ser Ser Leu Ala Ser
1               5

<210> SEQ ID NO 40
<211> LENGTH: 7
<212> TYPE: PRT
<213> ORGANISM: Artificial Sequence
<220> FEATURE:
<223> OTHER INFORMATION: recombinant chimeric antibody

<400> SEQUENCE: 40

Ser Ala Ser Thr Leu Ala Ser
1               5

<210> SEQ ID NO 41
<211> LENGTH: 7
<212> TYPE: PRT
<213> ORGANISM: Artificial Sequence
<220> FEATURE:
<223> OTHER INFORMATION: recombinant chimeric antibody

<400> SEQUENCE: 41

Ser Ala Ser Thr Leu Ala Ser
1               5

<210> SEQ ID NO 42
<211> LENGTH: 7
<212> TYPE: PRT
<213> ORGANISM: Artificial Sequence
<220> FEATURE:
<223> OTHER INFORMATION: recombinant chimeric antibody
```

```
<400> SEQUENCE: 42

Lys Ala Ser Thr Leu Glu Ser
1               5

<210> SEQ ID NO 43
<211> LENGTH: 12
<212> TYPE: PRT
<213> ORGANISM: Artificial Sequence
<220> FEATURE:
<223> OTHER INFORMATION: recombinant chimeric antibody

<400> SEQUENCE: 43

Gln Cys Ser Ala Tyr Gly Ser Arg Tyr Val Gly Gly
1               5                   10

<210> SEQ ID NO 44
<211> LENGTH: 12
<212> TYPE: PRT
<213> ORGANISM: Artificial Sequence
<220> FEATURE:
<223> OTHER INFORMATION: recombinant chimeric antibody

<400> SEQUENCE: 44

Gln Cys Ser Ala Tyr Gly Ser Val Tyr Val Gly Thr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: recombinant chimeric antibody

<400> SEQUENCE: 45

Gln Cys Thr Asp Val Gly Ser Asn Tyr Leu Gly Ala
1               5                   10

<210> SEQ ID NO 46
<211> LENGTH: 12
<212> TYPE: PRT
<213> ORGANISM: Artificial Sequence
<220> FEATURE:
<223> OTHER INFORMATION: recombinant chimeric antibody

<400> SEQUENCE: 46

Gln Cys Thr Ala Ala Gly Ser Val Ser Val Gly Ala
1               5                   10

<210> SEQ ID NO 47
<211> LENGTH: 14
<212> TYPE: PRT
<213> ORGANISM: Artificial Sequence
<220> FEATURE:
<223> OTHER INFORMATION: recombinant chimeric antibody

<400> SEQUENCE: 47

Gln Asn Asn Asn Gly Gly Ser Tyr Ser Ser Ala Phe Gly Ala
1               5                   10

<210> SEQ ID NO 48
<211> LENGTH: 14
<212> TYPE: PRT
<213> ORGANISM: Artificial Sequence
<220> FEATURE:
<223> OTHER INFORMATION: recombinant chimeric antibody
```

```
<400> SEQUENCE: 48

Gln Ser Asn Tyr Gly Ser Gly Ser Ser Trp Glu Gly Ala
1               5                   10

<210> SEQ ID NO 49
<211> LENGTH: 29
<212> TYPE: PRT
<213> ORGANISM: Artificial Sequence
<220> FEATURE:
<223> OTHER INFORMATION: recombinant chimeric antibody

<400> SEQUENCE: 49

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25

<210> SEQ ID NO 50
<211> LENGTH: 29
<212> TYPE: PRT
<213> ORGANISM: Artificial Sequence
<220> FEATURE:
<223> OTHER INFORMATION: recombinant chimeric antibody

<400> SEQUENCE: 50

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25

<210> SEQ ID NO 51
<211> LENGTH: 29
<212> TYPE: PRT
<213> ORGANISM: Artificial Sequence
<220> FEATURE:
<223> OTHER INFORMATION: recombinant chimeric antibody

<400> SEQUENCE: 51

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25

<210> SEQ ID NO 52
<211> LENGTH: 29
<212> TYPE: PRT
<213> ORGANISM: Artificial Sequence
<220> FEATURE:
<223> OTHER INFORMATION: recombinant chimeric antibody

<400> SEQUENCE: 52

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25

<210> SEQ ID NO 53
<211> LENGTH: 29
<212> TYPE: PRT
<213> ORGANISM: Artificial Sequence
<220> FEATURE:
<223> OTHER INFORMATION: recombinant chimeric antibody

<400> SEQUENCE: 53
```

-continued

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser
            20                  25

<210> SEQ ID NO 54
<211> LENGTH: 29
<212> TYPE: PRT
<213> ORGANISM: Artificial Sequence
<220> FEATURE:
<223> OTHER INFORMATION: recombinant chimeric antibody

<400> SEQUENCE: 54

Gln Ser Leu Glu Glu Ser Gly Gly Asp Leu Val Lys Pro Gly Ala Ser
1               5                   10                  15
Leu Thr Leu Thr Cys Thr Ala Ser Gly Phe Ser Phe Ser
            20                  25

<210> SEQ ID NO 55
<211> LENGTH: 14
<212> TYPE: PRT
<213> ORGANISM: Artificial Sequence
<220> FEATURE:
<223> OTHER INFORMATION: recombinant chimeric antibody

<400> SEQUENCE: 55

Trp Val Arg Gln Ala Pro Gly Lys Gly Leu Glu Trp Ile Gly
1               5                   10

<210> SEQ ID NO 56
<211> LENGTH: 14
<212> TYPE: PRT
<213> ORGANISM: Artificial Sequence
<220> FEATURE:
<223> OTHER INFORMATION: recombinant chimeric antibody

<400> SEQUENCE: 56

Trp Val Arg Gln Ala Pro Gly Glu Gly Leu Glu Tyr Ile Gly
1               5                   10

<210> SEQ ID NO 57
<211> LENGTH: 14
<212> TYPE: PRT
<213> ORGANISM: Artificial Sequence
<220> FEATURE:
<223> OTHER INFORMATION: recombinant chimeric antibody

<400> SEQUENCE: 57

Trp Val Arg Gln Ala Pro Gly Lys Gly Leu Glu Trp Ile Gly
1               5                   10

<210> SEQ ID NO 58
<211> LENGTH: 14
<212> TYPE: PRT
<213> ORGANISM: Artificial Sequence
<220> FEATURE:
<223> OTHER INFORMATION: recombinant chimeric antibody

<400> SEQUENCE: 58

Trp Val Arg Gln Ala Pro Gly Lys Gly Leu Glu Tyr Ile Gly
1               5                   10

<210> SEQ ID NO 59
<211> LENGTH: 14
<212> TYPE: PRT
<213> ORGANISM: Artificial Sequence
```

```
<220> FEATURE:
<223> OTHER INFORMATION: recombinant chimeric antibody

<400> SEQUENCE: 59

Trp Val Arg Gln Ala Pro Gly Lys Gly Leu Glu Trp Ile Gly
1               5                   10

<210> SEQ ID NO 60
<211> LENGTH: 14
<212> TYPE: PRT
<213> ORGANISM: Artificial Sequence
<220> FEATURE:
<223> OTHER INFORMATION: recombinant chimeric antibody

<400> SEQUENCE: 60

Trp Leu Arg Gln Ala Pro Gly Lys Gly Leu Glu Trp Val Ala
1               5                   10

<210> SEQ ID NO 61
<211> LENGTH: 30
<212> TYPE: PRT
<213> ORGANISM: Artificial Sequence
<220> FEATURE:
<223> OTHER INFORMATION: recombinant chimeric antibody

<400> SEQUENCE: 61

Arg Phe Thr Ile Ser Lys Thr Ser Thr Val Asp Leu Lys Met Thr
1               5                   10                  15

Ser Pro Thr Thr Glu Asp Thr Ala Thr Tyr Phe Cys Ala Arg
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: recombinant chimeric antibody

<400> SEQUENCE: 62

Arg Ile Thr Ile Ser Lys Thr Ser Thr Val Asp Leu Lys Ile Ser
1               5                   10                  15

Ser Pro Thr Ala Glu Asp Thr Ala Thr Tyr Phe Cys Ala Arg
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: recombinant chimeric antibody

<400> SEQUENCE: 63

Arg Phe Thr Ile Ser Arg Thr Ser Thr Val Asp Leu Lys Met Thr
1               5                   10                  15

Ser Leu Thr Thr Glu Asp Thr Ala Thr Tyr Phe Cys Ala Arg
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: recombinant chimeric antibody

<400> SEQUENCE: 64
```

Arg Phe Thr Ile Ser Lys Thr Ser Thr Val Asp Leu Lys Ile Thr
1               5                   10                  15

Ser Pro Thr Thr Lys Asp Thr Ala Thr Tyr Phe Cys Ala Arg
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: recombinant chimeric antibody

<400> SEQUENCE: 65

Arg Phe Thr Ile Ser Lys Thr Ser Thr Val Asp Leu Lys Ile Thr
1               5                   10                  15

Ser Pro Thr Thr Glu Asp Thr Ala Thr Tyr Phe Cys Ala Arg
            20                  25                  30

<210> SEQ ID NO 66
<211> LENGTH: 31
<212> TYPE: PRT
<213> ORGANISM: Artificial Sequence
<220> FEATURE:
<223> OTHER INFORMATION: recombinant chimeric antibody

<400> SEQUENCE: 66

Arg Phe Thr Ile Ser Lys Thr Ser Ser Thr Thr Val Thr Leu Gln Met
1               5                   10                  15

Thr Ser Leu Thr Ala Ala Asp Thr Ala Thr Tyr Phe Cys Ala Arg
            20                  25                  30

<210> SEQ ID NO 67
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 67

Trp Gly Gln Gly Met Leu Val Thr Val Ser Ser
1               5                   10

<210> SEQ ID NO 68
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 68

Trp Gly Pro Gly Thr Leu Val Thr Val Ser Ser
1               5                   10

<210> SEQ ID NO 69
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 69

Trp Gly Gln Gly Thr Leu Val Thr Val Ser Ser
1               5                   10

<210> SEQ ID NO 70

```
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 70

Trp Gly Gln Gly Thr Leu Val Thr Val Ser Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 71

Trp Gly Pro Gly Thr Leu Val Thr Val Ser Ser
1               5                   10

<210> SEQ ID NO 72
<211> LENGTH: 11
<212> TYPE: PRT
<213> ORGANISM: Artificial Sequence
<220> FEATURE:
<223> OTHER INFORMATION: recombinant chimeric antibody

<400> SEQUENCE: 72

Trp Gly Pro Gly Thr Leu Val Thr Val Ser Ser
1               5                   10

<210> SEQ ID NO 73
<211> LENGTH: 23
<212> TYPE: PRT
<213> ORGANISM: Artificial Sequence
<220> FEATURE:
<223> OTHER INFORMATION: recombinant chimeric antibody

<400> SEQUENCE: 73

Asp Ile Val Met Thr Gln Thr Pro Ala Ser Val Glu Ala Ala Val Gly
1               5                   10                  15

Gly Thr Val Thr Ile Lys Cys
            20

<210> SEQ ID NO 74
<211> LENGTH: 23
<212> TYPE: PRT
<213> ORGANISM: Artificial Sequence
<220> FEATURE:
<223> OTHER INFORMATION: recombinant chimeric antibody

<400> SEQUENCE: 74

Asp Val Val Met Thr Gln Thr Pro Ala Ser Val Ser Glu Pro Val Gly
1               5                   10                  15

Gly Thr Val Thr Ile Lys Cys
            20

<210> SEQ ID NO 75
<211> LENGTH: 23
<212> TYPE: PRT
<213> ORGANISM: Artificial Sequence
<220> FEATURE:
<223> OTHER INFORMATION: recombinant chimeric antibody

<400> SEQUENCE: 75
```

```
Asp Val Val Met Thr Gln Thr Pro Ala Ser Val Ser Glu Pro Val Gly
1               5                   10                  15

Gly Thr Val Thr Ile Lys Cys
            20
```

<210> SEQ ID NO 76
<211> LENGTH: 23
<212> TYPE: PRT
<213> ORGANISM: Artificial Sequence
<220> FEATURE:
<223> OTHER INFORMATION: recombinant chimeric antibody

<400> SEQUENCE: 76

```
Asp Ile Val Met Thr Gln Thr Pro Ala Ser Val Ser Glu Pro Val Gly
1               5                   10                  15

Gly Thr Val Thr Ile Lys Cys
            20
```

<210> SEQ ID NO 77
<211> LENGTH: 23
<212> TYPE: PRT
<213> ORGANISM: Artificial Sequence
<220> FEATURE:
<223> OTHER INFORMATION: recombinant chimeric antibody

<400> SEQUENCE: 77

```
Asp Pro Val Leu Thr Gln Thr Pro Ser Ser Ala Ser Glu Pro Val Gly
1               5                   10                  15

Gly Thr Val Thr Ile Lys Cys
            20
```

<210> SEQ ID NO 78
<211> LENGTH: 23
<212> TYPE: PRT
<213> ORGANISM: Artificial Sequence
<220> FEATURE:
<223> OTHER INFORMATION: recombinant chimeric antibody

<400> SEQUENCE: 78

```
Asp Ile Val Met Thr Gln Thr Pro Ser Ser Val Ser Glu Pro Val Gly
1               5                   10                  15

Gly Thr Val Thr Ile Lys Cys
            20
```

<210> SEQ ID NO 79
<211> LENGTH: 15
<212> TYPE: PRT
<213> ORGANISM: Artificial Sequence
<220> FEATURE:
<223> OTHER INFORMATION: recombinant chimeric antibody

<400> SEQUENCE: 79

```
Trp Tyr Gln Gln Lys Pro Gly Gln Arg Pro Lys Leu Leu Ile Tyr
1               5                   10                  15
```

<210> SEQ ID NO 80
<211> LENGTH: 15
<212> TYPE: PRT
<213> ORGANISM: Artificial Sequence
<220> FEATURE:
<223> OTHER INFORMATION: recombinant chimeric antibody

<400> SEQUENCE: 80

```
Trp Tyr Gln Gln Lys Pro Gly Gln Pro Pro Lys Leu Leu Ile Tyr
1               5                   10                  15
```

<210> SEQ ID NO 81
<211> LENGTH: 15
<212> TYPE: PRT
<213> ORGANISM: Artificial Sequence
<220> FEATURE:
<223> OTHER INFORMATION: recombinant chimeric antibody

<400> SEQUENCE: 81

Trp Tyr Gln Gln Lys Pro Gly Gln Arg Pro Lys Leu Leu Met Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: recombinant chimeric antibody

<400> SEQUENCE: 82

Trp Tyr Gln Gln Lys Pro Gly Gln Arg Pro Lys Leu Leu Ile Tyr
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: recombinant chimeric antibody

<400> SEQUENCE: 83

Trp Tyr Gln Gln Lys Pro Gly Gln Pro Pro Glu Leu Leu Ile Tyr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: recombinant chimeric antibody

<400> SEQUENCE: 84

Trp Tyr Gln Gln Lys Pro Gly Gln Pro Pro Lys Arg Leu Ile Tyr
1               5                   10                  15

<210> SEQ ID NO 85
<211> LENGTH: 32
<212> TYPE: PRT
<213> ORGANISM: Artificial Sequence
<220> FEATURE:
<223> OTHER INFORMATION: recombinant chimeric antibody

<400> SEQUENCE: 85

Gly Val Pro Ser Arg Phe Lys Gly Ser Gly Ser Gly Thr Glu Tyr Thr
1               5                   10                  15

Leu Thr Ile Ser Asp Leu Glu Ser Gly Asp Ala Ala Thr Tyr Tyr Cys
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: recombinant chimeric antibody

<400> SEQUENCE: 86

Gly Val Ser Ser Arg Phe Arg Gly Ser Arg Ser Gly Thr Glu Phe Thr
1               5                   10                  15

Leu Thr Ile Ser Asp Leu Glu Ser Ala Asp Ala Ala Tyr Tyr Cys
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: recombinant chimeric antibody

<400> SEQUENCE: 87

Gly Val Ser Ser Arg Phe Lys Gly Ser Arg Ser Gly Thr Glu Tyr Thr
1               5                   10                  15

Leu Thr Ile Ser Asp Leu Glu Cys Ala Asp Ala Ala Tyr Tyr Cys
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: recombinant chimeric antibody

<400> SEQUENCE: 88

Gly Val Ser Ser Arg Phe Lys Gly Ser Gly Ser Gly Thr Gln Phe Thr
1               5                   10                  15

Leu Thr Ile Ser Asp Leu Glu Cys Ala Asp Ala Ala Tyr Tyr Cys
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: recombinant chimeric antibody

<400> SEQUENCE: 89

Gly Val Pro Ser Arg Phe Lys Gly Ser Gly Ser Gly Thr Gln Phe Thr
1               5                   10                  15

Leu Thr Ile Ser Asp Leu Glu Cys Ala Asp Ser Ala Thr Tyr Tyr Cys
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: recombinant chimeric antibody

<400> SEQUENCE: 90

Gly Val Pro Ser Arg Phe Lys Gly Ser Gly Ser Gly Thr Glu Phe Thr
1               5                   10                  15

Leu Thr Ile Ser Asp Leu Glu Cys Ala Asp Ala Ala Thr Tyr Tyr Cys
            20                  25                  30

<210> SEQ ID NO 91
<211> LENGTH: 10
<212> TYPE: PRT
<213> ORGANISM: Artificial Sequence
<220> FEATURE:
<223> OTHER INFORMATION: recombinant chimeric antibody

<400> SEQUENCE: 91

```
Phe Gly Gly Gly Thr Glu Val Val Val Lys
1               5                   10

<210> SEQ ID NO 92
<211> LENGTH: 10
<212> TYPE: PRT
<213> ORGANISM: Artificial Sequence
<220> FEATURE:
<223> OTHER INFORMATION: recombinant chimeric antibody

<400> SEQUENCE: 92

Phe Gly Gly Gly Thr Glu Val Val Val Lys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: recombinant chimeric antibody

<400> SEQUENCE: 93

Phe Gly Gly Gly Thr Glu Val Val Val Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: recombinant chimeric antibody

<400> SEQUENCE: 94

Phe Gly Gly Gly Thr Glu Val Val Val Asn
1               5                   10

<210> SEQ ID NO 95
<211> LENGTH: 10
<212> TYPE: PRT
<213> ORGANISM: Artificial Sequence
<220> FEATURE:
<223> OTHER INFORMATION: recombinant chimeric antibody

<400> SEQUENCE: 95

Phe Gly Gly Gly Thr Glu Val Val Val Lys
1               5                   10

<210> SEQ ID NO 96
<211> LENGTH: 10
<212> TYPE: PRT
<213> ORGANISM: Artificial Sequence
<220> FEATURE:
<223> OTHER INFORMATION: recombinant chimeric antibody

<400> SEQUENCE: 96

Phe Gly Gly Gly Thr Glu Val Val Val Lys
1               5                   10

<210> SEQ ID NO 97
<211> LENGTH: 107
<212> TYPE: PRT
<213> ORGANISM: Homo sapiens

<400> SEQUENCE: 97

Arg Thr Val Ala Ala Pro Ser Val Phe Ile Phe Pro Pro Ser Asp Glu
1               5                   10                  15
```

```
Gln Leu Lys Ser Gly Thr Ala Ser Val Cys Leu Leu Asn Asn Phe
         20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
             100                 105

<210> SEQ ID NO 98
<211> LENGTH: 329
<212> TYPE: PRT
<213> ORGANISM: Homo sapiens

<400> SEQUENCE: 98

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
 130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 99
<211> LENGTH: 331
<212> TYPE: PRT
<213> ORGANISM: Homo sapiens

<400> SEQUENCE: 99

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Pro Lys Ser Cys Asp Lys Thr His Thr Cys Pro Pro
            100                 105                 110
Cys Pro Ala Pro Glu Leu Leu Gly Gly Pro Ser Val Phe Leu Phe Pro
        115                 120                 125
Pro Lys Pro Lys Asp Thr Leu Met Ile Ser Arg Thr Pro Glu Val Thr
    130                 135                 140
Cys Val Val Val Asp Val Ser His Glu Asp Pro Glu Val Lys Phe Asn
145                 150                 155                 160
Trp Tyr Val Asp Gly Val Glu Val His Asn Ala Lys Thr Lys Pro Arg
                165                 170                 175
Glu Glu Gln Tyr Asn Ser Thr Tyr Arg Val Val Ser Val Leu Thr Val
            180                 185                 190
Leu His Gln Asp Trp Leu Asn Gly Lys Glu Tyr Lys Cys Lys Val Ser
        195                 200                 205
Asn Lys Ala Leu Pro Ala Pro Ile Glu Lys Thr Ile Ser Lys Ala Lys
    210                 215                 220
Gly Gln Pro Arg Glu Pro Gln Val Tyr Thr Leu Pro Pro Ser Arg Asp
225                 230                 235                 240
Glu Leu Thr Lys Asn Gln Val Ser Leu Thr Cys Leu Val Lys Gly Phe
                245                 250                 255
Tyr Pro Ser Asp Ile Ala Val Glu Trp Glu Ser Asn Gly Gln Pro Glu
            260                 265                 270
Asn Asn Tyr Lys Thr Thr Pro Pro Val Leu Asp Ser Asp Gly Ser Phe
        275                 280                 285
Phe Leu Tyr Ser Lys Leu Thr Val Asp Lys Ser Arg Trp Gln Gln Gly
    290                 295                 300
Asn Val Phe Ser Cys Ser Val Met His Glu Ala Leu His Asn His Tyr
305                 310                 315                 320
```

Thr Gln Lys Ser Leu Ser Leu Ser Pro Gly Lys
            325                 330

<210> SEQ ID NO 100
<211> LENGTH: 119
<212> TYPE: PRT
<213> ORGANISM: Artificial Sequence
<220> FEATURE:
<223> OTHER INFORMATION: humanized VR

<400> SEQUENCE: 100

Gln Val Gln Leu Glu Glu Ser Gly Gly Arg Val Val Gln Pro Gly Thr
1               5                   10                  15

Ser Leu Arg Leu Ser Cys Ala Ala Ser Gly Phe Ser Leu Ser Asn Tyr
            20                  25                  30

Gly Val Ser Trp Val Arg Gln Ala Pro Gly Lys Gly Leu Glu Tyr Val
        35                  40                  45

Ala Ile Ile Ser Gly Ser Gly Phe Thr Tyr Tyr Ala Ser Trp Ala Lys
    50                  55                  60

Gly Arg Phe Thr Ile Ser Lys Asp Thr Ser Lys Asn Thr Val Val Met
65                  70                  75                  80

Gln Met Thr Ser Leu Arg Ala Glu Asp Thr Ala Thr Tyr Phe Cys Ala
                85                  90                  95

Arg Gly Val Val Pro Gly Tyr Asn Ala Gly Gly Leu Trp Gly Gln Gly
            100                 105                 110

Thr Leu Val Thr Val Ser Ser
        115

<210> SEQ ID NO 101
<211> LENGTH: 119
<212> TYPE: PRT
<213> ORGANISM: Artificial Sequence
<220> FEATURE:
<223> OTHER INFORMATION: humanized VR

<400> SEQUENCE: 101

Glu Glu His Leu Glu Glu Ser Gly Gly Arg Leu Val Lys Pro Gly Thr
1               5                   10                  15

Ser Leu Arg Leu Ser Cys Thr Val Ser Gly Phe Ser Leu Ser Asn Tyr
            20                  25                  30

Gly Val Ser Trp Val Arg Gln Ala Pro Gly Arg Gly Leu Glu Tyr Val
        35                  40                  45

Ser Ile Ile Ser Gly Ser Gly Phe Thr Tyr Tyr Ala Ser Trp Ala Lys
    50                  55                  60

Gly Arg Phe Thr Ile Ser Lys Asp Thr Ala Arg Asp Ser Val Tyr Leu
65                  70                  75                  80

Gln Met Asn Ser Leu Arg Ala Glu Asp Thr Ala Thr Tyr Phe Cys Ala
                85                  90                  95

Arg Gly Val Val Pro Gly Tyr Asn Ala Gly Gly Leu Trp Gly Gln Gly
            100                 105                 110

Thr Leu Val Thr Val Ser Ser
        115

<210> SEQ ID NO 102
<211> LENGTH: 110
<212> TYPE: PRT
<213> ORGANISM: Artificial Sequence
<220> FEATURE:
<223> OTHER INFORMATION: humanized VR

```
<400> SEQUENCE: 102

Asp Ile Gln Met Thr Gln Ser Pro Ser Ser Leu Ser Ala Ser Val Gly
1               5                   10                  15

Asp Arg Ile Thr Ile Thr Cys Gln Ala Ser Gln Gly Ile Ser Thr Ala
            20                  25                  30

Leu Ala Trp Tyr Gln Gln Lys Pro Gly Gln Val Pro Lys Leu Leu Ile
        35                  40                  45

Tyr Ser Ala Ser Thr Leu Ala Ser Gly Val Pro Ser Arg Phe Lys Gly
50                  55                  60

Ser Gly Ser Gly Thr Glu Phe Thr Leu Thr Ile Ser Ser Leu Gln Ala
65                  70                  75                  80

Glu Asp Val Ala Thr Tyr Tyr Cys Gln Cys Thr Ala Ala Gly Ser Val
                85                  90                  95

Ser Val Gly Ala Phe Gly Gly Gly Thr Glu Val Val Ile Lys
            100                 105                 110

<210> SEQ ID NO 103
<211> LENGTH: 110
<212> TYPE: PRT
<213> ORGANISM: Artificial Sequence
<220> FEATURE:
<223> OTHER INFORMATION: humanized VR

<400> SEQUENCE: 103

Asp Ile Val Met Thr Gln Ser Pro Ser Ser Val Ser Ala Ser Val Gly
1               5                   10                  15

Asp Arg Val Thr Ile Thr Cys Gln Ala Ser Gln Gly Ile Ser Thr Ala
            20                  25                  30

Leu Ala Trp Tyr Gln Gln Lys Pro Gly Gln Ala Pro Lys Leu Leu Ile
        35                  40                  45

Tyr Ser Ala Ser Thr Leu Ala Ser Gly Val Pro Ser Arg Phe Lys Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Cys Thr Ala Ala Gly Ser Val
                85                  90                  95

Ser Val Gly Ala Phe Gly Gln Gly Thr Glu Leu Val Ile Lys
            100                 105                 110

<210> SEQ ID NO 104
<211> LENGTH: 110
<212> TYPE: PRT
<213> ORGANISM: Artificial Sequence
<220> FEATURE:
<223> OTHER INFORMATION: humanized VR

<400> SEQUENCE: 104

Asp Ile Glu Leu Thr Gln Ser Pro Ser Ser Val Ser Ala Ser Val Gly
1               5                   10                  15

Asp Arg Val Thr Ile Thr Cys Gln Ala Ser Gln Gly Ile Ser Thr Ala
            20                  25                  30

Leu Ala Trp Tyr Gln Gln Lys Pro Gly Gln Ala Pro Lys Leu Leu Ile
        35                  40                  45

Tyr Ser Ala Ser Thr Leu Ala Ser Gly Val Pro Ser Arg Phe Lys Gly
50                  55                  60

Ser Gly Ser Gly Thr Asp Phe Thr Leu Thr Ile Ser Ser Leu Gln Ser
65                  70                  75                  80
```

```
Glu Asp Ser Ala Thr Tyr Tyr Cys Gln Cys Thr Ala Ala Gly Ser Val
                85                  90                  95

Ser Val Gly Ala Phe Gly Gly Gly Thr Lys Val Val Ile Glu
            100             105                 110
```